(12) United States Patent
Swift

(10) Patent No.: US 6,686,440 B2
(45) Date of Patent: Feb. 3, 2004

(54) COMOMER COMPOSITIONS FOR PRODUCTION OF IMIDE-CONTAINING POLYAMINO ACIDS

(75) Inventor: Graham Swift, Chapel Hill, NC (US)

(73) Assignee: Folia, Inc., Birmingham, AL (US)

( * ) Notice: Subject to any disclaimer, the term of this patent is extended or adjusted under 35 U.S.C. 154(b) by 0 days.

(21) Appl. No.: 10/307,349

(22) Filed: Dec. 2, 2002

(65) Prior Publication Data

US 2003/0125510 A1 Jul. 3, 2003

Related U.S. Application Data

(63) Continuation of application No. 09/776,897, filed on Feb. 6, 2001, now Pat. No. 6,495,658.

(51) Int. Cl.[7] .............................................. C08G 63/44
(52) U.S. Cl. ....................................... 528/363; 528/328
(58) Field of Search ................................. 528/363, 328

(56) References Cited

U.S. PATENT DOCUMENTS

| | | |
|---|---|---|
| 4,866,161 A | 9/1989 | Sikes et al. |
| 4,868,287 A | 9/1989 | Sikes et al. |
| 5,051,401 A | 9/1991 | Sikes |
| 5,247,068 A | 9/1993 | Donachy et al. |
| 5,260,272 A | 11/1993 | Donachy et al. |
| 5,371,180 A | 12/1994 | Groth et al. |
| 5,548,036 A | 8/1996 | Kroner et al. |
| 5,639,832 A | 6/1997 | Kroner et al. |
| 5,773,564 A | 6/1998 | Sikes |
| 5,902,357 A | 5/1999 | Riegels et al. |
| 5,936,121 A | 8/1999 | Gelosa et al. |
| 5,955,549 A | 9/1999 | Chang et al. |
| 5,981,691 A | 11/1999 | Sikes |
| 6,027,804 A | 2/2000 | Chou et al. |
| 6,136,950 A | 10/2000 | Vickers, Jr. et al. |
| 6,160,110 A | 12/2000 | Thomaides et al. |
| 6,254,644 B1 | 7/2001 | Traubel et al. |
| 6,306,378 B1 | 10/2001 | Guth et al. |

FOREIGN PATENT DOCUMENTS

| | | |
|---|---|---|
| EP | 0 980 883 A1 | 2/2000 |
| EP | 1 120 433 A1 | 1/2001 |
| WO | WO 98/47964 | 10/1998 |
| WO | WO 00/00536 | 1/2000 |

OTHER PUBLICATIONS

Wang Yaquan (CN), Direct polyaspartate synthesizing process catalyzed by aspartic acid precursor, Sep. 27, 2000, Abstract of Patent No. CN1267673.
J. Hofmann, Abstract of Patent No. DE 4323191, Jan. 12, 1995.
H. Feindt, Abstract of Patent No. DE 4427233, Jan. 4, 1996.
J.J. Guth, Abstract of Patent No. WO 200059459, Oct. 12, 2000.

Primary Examiner—Terressa M. Boykin
(74) Attorney, Agent, or Firm—Stamatios Mylonakis

(57) ABSTRACT

Described are monomer compositions containing aspartic acid and other comonomers, such as monosodium aspartate, and methods for their production. The monomer compositions can be polymerized, particularly by thermal polymerization, to obtain useful and novel imide-containing polyamino acids, i.e., copolymers containing polymerized aspartate units and succinimide units. The invention is also directed to the resulting polymeric materials, their methods of production, and their uses. Uses of the imide-containing polyamino acids include, for example, dispersants in detergents and cleansers, water-treatment chemicals as antiscalants and corrosion inhibitors, personal-care additives for softening and moisturizing, and many others.

42 Claims, 17 Drawing Sheets

COMOMER COMPOSITIONS FOR PRODUCTION OF IMIDE-CONTAINING POLYAMINO ACIDS

This application is a continuation of application Ser. No. 09/776,897, filed Feb. 6, 2001 now U.S. Pat. No. 6,495,658 which is incorporated herein by reference in its entirety.

The present invention includes monomer compositions containing aspartic acid and other comonomers, such as monosodium aspartate, and methods for their production. The monomer compositions can be polymerized, particularly by thermal polymerization, to obtain useful and novel imide-containing polyamino acids, i.e., copolymers containing polymerized aspartic acid or aspartate units and succinimide units. Thus, the invention is also directed to the resulting polymeric materials, their methods of production, and their uses as described herein. Uses of the imide-containing polyamino acids include, for example, dispersants in detergents and cleansers, water-treatment chemicals as anti-scalants and corrosion inhibitors, personal-care additives for softening and moisturizing, and many others.

BACKGROUND OF THE INVENTION

Aspartic acid has been produced commercially since the 1980's via immobilized enzyme methods. The aspartic acid so produced mainly has been used as a component of the synthetic sweetener, N-aspartyl phenylalanine methyl ester (ASPARTAME®).

In a typical production pathway, a solution of ammonium maleate is converted to fumarate via action of an immobilized enzyme, maleate isomerase, by continuous flow over an immobilized enzyme bed. Next, the solution of ammonium fumarate is treated also by continuous flow of the solution over a bed of the immobilized enzyme, aspartase. A relatively concentrated solution of ammonium aspartate is produced, which then is treated with an acid, for example nitric acid, to precipitate aspartic acid. After drying, the resultant product of the process is powdered or crystalline L-aspartic acid. Prior art that exemplifies this production pathway includes U.S. Pat. No. 4,560,653 to Sherwin and Blouin (1985), U.S. Pat. No. 5,541,090 to Sakano et al. (1996), and U.S. Pat. No. 5,741,681 to Kato et al. (1998).

In addition, nonenzymatic, chemical routes to D,L aspartic acid via treatment of maleic acid, fumaric acid, or their mixtures with ammonia at elevated temperature have been known for over 150 years (see Harada, K., *Polycondensation of thermal precursors of aspartic acid. Journal of Organic Chemistry* 24, 1662–1666 (1959); also. U.S. Pat. No. 5,872,285 to Mazo et al. (1999)). Although the nonenzymatic routes are significantly less quantitative than the enzymatic syntheses of aspartic acid, possibilities for continuous processes and recycling of reactants and by-products via chemical routes are envisioned.

Polymerization and copolymerization of aspartic acid alone or with other comonomers is known. As reviewed in U.S. Pat. No. 5,981,691 to Sikes (1999), synthetic work with polyamino acids, beginning with the homopolymer of aspartic acid, dates to the mid 1800's and has continued to the present. Interest in polyaspartates and related molecules increased in the mid 1980's; awareness of the commercial potential of these molecules grew. Particular attention has been paid to biodegradable and environmentally compatible polyaspartates for commodity uses such as detergent additives and superabsorbent materials in disposable diapers, although numerous other uses have been contemplated, ranging from water-treatment additives for control of scale and corrosion to anti-tartar agents in toothpastes.

There have been some teachings of producing copolymers of succinimide and aspartic acid or aspartate via thermal polymerization of maleic acid plus ammonia or ammonia compounds. For example, U.S. Pat. No. 5,548,036 to Kroner et al.(1996) taught that polymerization at less than 140° C. resulted in aspartic acid residue-containing polysuccinimides. However, the reason that some aspartic acid residues persisted in the product polymers was that the temperatures of polymerization were too low to drive the reaction to completion, leading to inefficient processes.

JP 8277329 (1996) to Tomida exemplified the thermal polymerization of potassium aspartate in the presence of 5 mole % and 30 mole % phosphoric acid. The purpose of the phosphoric acid was stated to serve as a catalyst so that molecules of higher molecular weight might be produced. However, the products of the reaction were of lower molecular weight than were produced in the absence of the phosphoric acid, indicating that there was no catalytic effect. There was no mention of producing copolymers of aspartate and succinimide; rather, there was mention of producing only homopolymers of polyaspartate. In fact, addition of phosphoric acid in this fashion to form a slurry or intimate mixture with the powder of potassium aspartate, is actually counterproductive to formation of copolymers containing succinimide and aspartic acid residue units, or to formation of the condensation amide bonds of the polymers in general. That is, although the phosphoric acid may act to generate some fraction of residues as aspartic acid, it also results in the occurrence of substantial amounts of phosphate anion in the slurry or mixture. Upon drying to form the salt of the intimate mixture, such anions bind ionically with the positively charged amine groups of aspartic acid and aspartate residues, blocking them from the polymerization reaction, thus resulting in polymers of lower molecular weight in lower yield.

Earlier, U.S. Pat. No. 5,371,180 to Groth et al. (1994) had demonstrated production of copolymers of succinimide and aspartate by thermal treatment of maleic acid plus ammonium compounds in the presence of alkaline carbonates. The invention involved an alkaline, ring-opening environment of polymerization such that some of the polymeric succinimide residues would be converted to the ring-opened, aspartate form. For this reason, only alkaline carbonates were taught and there was no mention of cations functioning themselves in any way to prevent imide formation.

More recently, U.S. Pat. No. 5,936,121 to Gelosa et al. (1999) taught formation of oligomers (Mw<1000) of aspartate having chain-terminating residues of unsaturated dicarboxylic compounds such as maleic and acrylic acids. These aspartic-rich compounds were formed via thermal condensation of mixtures of sodium salts of maleic acid plus ammonium/sodium maleic salts that were dried from solutions of ammonium maleate to which NaOH had been added. They were producing compounds to sequester alkaline-earth metals. In addition, the compounds were shown to be nontoxic and biodegradable by virtue of their aspartic acid composition. Moreover, the compounds retained their biodegradability by virtue of their very low Mw, notwithstanding the presence of the chain-terminating residues, which when polymerized with themselves to sizes above the oligomeric size, resulted in non-degradable polymers.

A number of reports and patents in the area of polyaspartics (i.e., poly(aspartic acid) or polyaspartate), polysuccinimides, and their derivatives have appeared more recently. Notable among these, for example, there have been disclosures of novel superabsorbents (U.S. Pat. No. 5,955, 549 to Chang and Swift, 1999; U.S. Pat. No. 6,027,804 to Chou et al., 2000), dye-leveling agents for textiles (U.S. Pat. No. 5,902,357 to Riegels et al., 1999), and solvent-free synthesis of sulfhydryl-containing corrosion and scale inhibitors (EP 0 980 883 to Oda. 2000). There also has been teaching of dye-transfer inhibitors prepared by nucleophilic addition of amino compounds to polysuccinimide suspended in water (U.S. Pat. No. 5,639,832 to Kroner et al. 1997), which reactions are inefficient due to the marked insolubility of polysuccinimide in water.

U.S. Pat. No. 5,981,691 purportedly introduced the concept of mixed amide/imide, water-soluble copolymers of aspartate and succinimide for a variety of uses. The concept therein was that a monocationic salt of aspartate when formed into a dry mixture with aspartic acid could be thermally polymerized to produce the water-soluble copoly (aspartate, succinimide). The theory was that the aspartic acid comonomer when polymerized led to succinimide residues in the product polymer and the monosodium aspartate comonomer led to aspartate residues in the product polymer. It was not recognized that merely providing the comonomers was not sufficient to obtain true copolymers and that certain other conditions were necessary to avoid obtaining primarily mixtures of polyaspartate and polysuccinimide copolymers. In U.S. Pat. No. 5,981,691, the comonomeric mixtures were formed from an aqueous slurry of aspartic acid, adjusted to specific values of pH, followed by drying. There was no teaching of use of solutions of ammonium aspartate or any other decomposable cation plus NaOH, or other forms of sodium or other cations, for generation of comonomeric compositions of aspartic acid and salts of aspartate. Thus, although some of the U.S. Pat. No. 5,981,691 examples obtain products containing some copolymer in mixture with other products, particularly homopolymers, as discussed in the Summary of the Invention below, the theory that true copolymers could be obtained merely by providing the comonomers in the manner taught in U.S. Pat. No. 5,981,691 was not fully realized.

Thus, to date, there have been no successful disclosures of water-soluble or wettable, mixed amide/imide polyamino acids such as copolymers of aspartate and succinimide or related imide-containing polyamino acids.

SUMMARY OF THE INVENTION

It has now been discovered that the methods taught in U.S. Pat. No. 5,981,691, or in any of the other discussed references, fail to provide an efficient process to produce a true mixed amide/imide polyamino acid copolymer, a copolymer prepared by such process or other novel copolymers. These previous references fail to teach a method whereby a sufficiently intimate mixture of the comonomers is provided such that polymerization leads to a true copolymer with a significant number of both aspartate and succinimide residues. For example, the above-described method of U.S. Pat. No. 5,981,691 purportedly for producing such copolymers results, instead in a mixture, albeit intimate mixture, of aspartic acid (amide) and succinimide (imide) homopolymers, possibly with an amount of copolymer, unappreciated by the reference, mixed therein. A method has now been discovered providing a sufficiently intimate mixture of the comonomers and, therefore, allowing the production of a true copolymer with a significant number of both aspartate (also referred to as amide) residues or units and succinimide (also referred to as imide) units or residues, as schematically shown by the following formula.

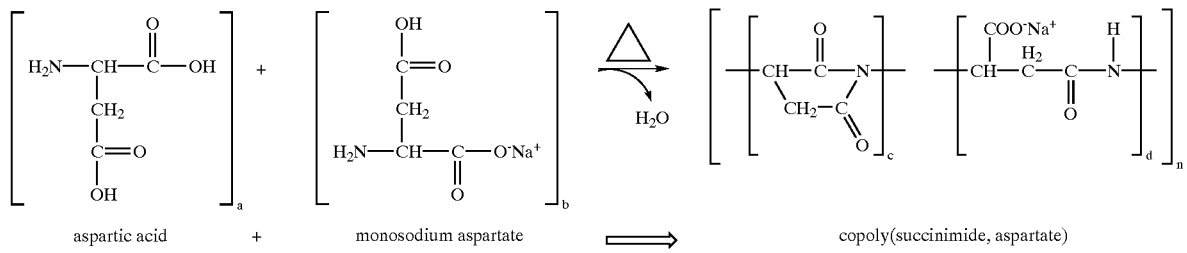

aspartic acid + monosodium aspartate ⟹ copoly(succinimide, aspartate)

The invention also can provide the resulting copolymers in isolated form. By isolated form it is meant that the copolymer is either: (a) in the substantial absence, e.g., less than 10%, preferably less than 5%, more particularly less than 1%, by weight of a polyaspartate or polysuccinimide homopolymer, (b) prepared by a method defined by this invention or (c) prepared by some other method not of this invention but which has a step of separating polyaspartate and/or polysuccinimide homopolymer from the copolymer.

Accordingly, the present invention teaches novel methods for producing mixed amide/imide copolymers of amino acids, as well as the resulting novel imide-containing polyamino acids themselves. Included are methods employing the monomers aspartic acid or aspartate salts having non-volatile or non-heat-decomposable cations. By aspartate or aspartate salt is meant a salt of the aspartate ion and any metallic cation, including alkali metal, alkaline earth metals or transition metals. Preferably the cations are alkali or alkaline earth metals, particularly Na, Mg, K, Ca, Rb, Sr, Cs and Ba, with sodium, magnesium, potassium and calcium, particularly sodium, being preferred. These monomers lead to amide formation. Other monomer, particularly aspartates having a volatile or heat-decomposable cation, preferably an ammonium or amine cation, lead to imide formation. In the following, the amide-generating cation will be represented by sodium ($Na^-$) and the imide-generating cation will be represented by ammonium ($NH_4^+$) but with the understanding that other cations creating the same effects for achieving the invention may be substituted. By volatile or heat-decomposable cation it is meant that the cation sufficiently dissociates from the aspartate anion under the giving drying conditions such that the remaining aspartate unit can cyclize to a succinimide unit during the polymerization. Cations which have at least 50% dissociation in this manner under the given drying conditions are considered volatile or heat-decomposable and cations which do not dissociate at least 50% are considered non-volatile or non-heat-decomposable.

In the present invention, some elements of the conventional, enzymatic processes for production of aspartic acid can be adapted for producing monomers useful in the invention. The production of the comonomer mixture, however, is a novel aspect. The method involves providing an intimate solution of an aspartate of a non-volatile cation and an aspartate of a volatile cation. By the term aspartate is meant an aspartic acid residue, either as a monomer or as a polymerized or copolymerized unit having its carboxyl group in ionic form associated with a cation, i.e., as —COO⁻. Specifically, for example, an ammonium aspartate solution can be titrated with NaOH to a fractional molar equivalence of a sodium salt of aspartate and an ammonium salt of aspartate. This comonomeric solution is then dried to produce a comonomer mixture of a partial sodium salt of aspartic acid and free aspartic acid. By free aspartic acid is meant aspartic acid or a polymerized or copolymerized aspartic acid residue having its carboxyl group not in ionic form, i.e. as —COOH. Because the dried comonomer mixture is prepared from the novel intimate solution of comonomers, an intimate dried mixture of these comonomers is obtained. Although not intending to be bound by this theory, it is believed that the mixture is intimate to the extent of exhibiting a salt lattice structure of the aspartate with the aspartic acid. It is possible for the dried comonomeric composition to also contain some residual ammonium aspartate, but in very small amounts, e.g., not exceeding 5% by weight, preferably not exceeding 2% by weight.

In effect, the aspartate of the volatile cation (e.g., ammonium) when dried from aqueous solution, is largely converted to powdered or crystalline aspartic acid. This is due to the loss of the decomposable cation, e.g., ammonia, as a vapor upon drying, with accompanying lowering of the pH of the evaporating solution as ammonia leaves the solution, for example, as a result of the following equilibrium being pulled to the left:

The sodium ion, on the other hand, has no significant vapor phase during drying and remains in the dried salt as a counter ion to aspartate monomers. Thus, the relative proportions of the comonomers, monosodium aspartate and aspartic acid, is set by the relative molar amounts of ammonium aspartate in solution and the NaOH added to the solution prior to drying.

The dried comonomer mixture is a clear, glassy solid if drying occurs in vacuo or in an oxygen-depleted atmosphere. In the presence of atmospheric oxygen, the dried comonomer preparation has a pale yellow, glassy appearance.

The comonomer composition of the present invention may also be prepared via nonenzymatic, chemical production of solutions of ammonium aspartate. For example, maleic acid plus ammonia in water plus heating, preferably at an elevated pressure, may produce ammonium aspartate in solution. Typically, temperatures of 80 to 160° C., preferably 120 to 160° C. and a pressure of up to about 120 psi can be used, although other conditions may be useful depending on the particular circumstances. Upon addition of the desired amount of NaOH, this solution is dried to form the comonomer composition containing the mixture of the sodium aspartate salt and aspartic acid.

The comonomeric composition may also be obtained via coprecipitation from solution. For example, addition of a hydrophobe or downward adjustment of pH may lead to coprecipitation of the monomers. These may then be isolated, for example by filtration, for use in the production of the imide-containing polymers.

Also included are methods in which maleic acid plus ammonia plus soluble, nonalkali as well as alkali, cationic salts are used to internally generate a combination of aspartic acid and monosodium aspartate comonomers for thermal polymerization to produce water-soluble, imide containing copolymers.

Upon polymerization, for example by thermal polycondensation, of the comonomer composition, any residual ammonia of the ammonium salt is further driven off as a vapor. The resulting product is a copolymer of sodium aspartate and succinimide units. Due to the novel comonomer dry mixture used to prepare this copolymer, a true copolymer is obtained with a significant amount of both of these amide and imide units. For example, it is preferred that such units are provided in the copolymer in a molar ratio of from 1:10 to 10:1, more preferably 1:5 to 5:1, particularly preferably 1:4 to 4:1 or at about 1:1. Exemplification of the ratios achievable is provided in the following Table 1.

TABLE 1

Titratable COOH groups of copolymers of aspartate and succinimide; the higher number of titratable COOH groups being indicative of a higher ration of aspartate units.

| Material | Titratable COOH Groups; μmoles-COOH per milligram of polymer | |
|---|---|---|
| | Theoretical | Actual (n = ≧ 4 ± st. dev.) |
| Polysuccinimide | <1.00 | 1.30 |
| Mono Na polyaspartate | 7.25 | 6.22 |
| Copoly (asp:suc) 5:1 | 6.04 | 6.22 ± 0.21 |
| Copoly (asp:suc) 4:1 | 5.80 | 5.41 ± 0.099 |
| Copoly (asp:suc) 3:1 | 5.43 | 5.23 ± 0.188 |
| Copoly (asp:suc) 2:1 | 4.78 | 4.80 ± 0.151 |
| Copoly (asp:suc) 1:1 | 3.62 | 3.52 ± 0.116 |
| Copoly (asp:suc) 1:2 | 2.51 | 2.66 ± 0.100 |
| Copoly (asp:suc) 1:3 | 1.81 | 2.07 ± 0.051 |
| Copoly (asp:suc) 1:4 | 1.45 | 1.72 ± 0.014 |

These copolymers exhibit advantageous properties, particularly advantageous water solubility properties, which makes them economically and ecologically advantageous for use in many applications. For example, they can provide biodegradeable polymers and polymers which can otherwise be adjusted to suit particular uses. Table 2 exemplifies some of the advantageous solubility properties of copolymers of the invention:

TABLE 2

| MATERIAL[1] | SOLUBILITY IN H₂O | SOLUBILITY IN 50% AQUEOUS ISOPROPANOL |
|---|---|---|
| Copoly (asp:suc) 1:1 | 90%[2] | 2.5% |
| Copoly (asp:suc) 1:2 | <30% | <2.5% |
| Copoly (asp:suc) 2:1 | 90% | 2.5% |
| Copoly (asp:suc) 3:1 | 90% | 2.5% |
| Copoly (asp:suc) 1:3 | <5% | Not Soluble |
| Copoly (asp:suc) 4:1 | 90% | 2.5% |
| Copoly (asp:suc) 1:4 | <5% | Not Soluble |
| Copoly (asp:suc) 5:1 | In aqueous alcoholic liquid laundry formulation[3]: >5.0% | |

[1]Copolymers prepared at 200° C., 4 hours.
[2]Weight/volume
[3]Liquid Tide

Additional comonomers may be added prior to the drying of the comonomer solution step to provide comonomeric feedstock for terpolymers and higher polymers of thermally condensed polyamino acids. In particular, the amino acids lysine and glutamate and salts thereof may be used. These can impart further water-solubility to the product imide-containing polymers. Moreover, other difunctional and multifunctional monomers such as aminocaproic acid and ornithine, as well as the other common amino acids including but not limited to alanine, glycine, leucine, isoleucine, methionine, and threonine; sugar-acids such as glucuronic acid; other hydroxyl-containing carboxylates such as citric acid and malonic acid; and other like molecules, are additional comonomers that would co-condense in the production of the imide-containing polyamino acids and may be useful to provide aqueous solubility and other useful properties to the imide-containing polyamino acids.

Accordingly, it is one object of the present invention to provide novel comonomeric compositions. It is another object of the present invention to provide methods of preparation of the novel comonomeric compositions. It is another object of the present invention to provide uses of the novel comonomeric compositions, particularly for copolymerization to prepare novel copolymers. It is another object of the present invention to provide novel imide-containing polyamino acids. It is another object of the present invention to provide methods of synthesis of the imide-containing, polyamino acids. It is another object of the present invention to provide methods of commercial manufacture of the imide-containing polyamino acids. It is another object of the present invention to provide methods of using, including commercial uses, of the imide-containing polyamino acids. This exemplification of objects of the invention is not a limitation and other objects and advantages of the invention are either explicitly or implicitly included in the disclosure as a whole, taking the knowledge of one of ordinary skill in the art into consideration.

Comonomeric compositions. The comonomeric compositions of the present invention can be prepared via the intimate solutions described above.

To prepare the starting solutions of aspartic acid and/or ammonium aspartate any current commercial process may be used. For example, dried powders or crystals of L-aspartic acid may be prepared by acid-precipitation of ammonium aspartate solutions such as occur as an intermediate stage of the immobilized enzyme route to aspartic acid.

Alternatively, aspartic acid for use in the present invention may be prepared chemically via addition of ammonia to maleic acid or fumaric acid plus heat, followed by acid precipitation of the aspartic acid zwitterion. Accordingly, either L-aspartic acid or D-aspartic acid may be used, or mixtures of L,D-aspartic acid may be used in this invention.

A novel and preferred method of preparation of the composition of comonomeric salts of the present invention is to add alkali to a concentrated solution of ammonium aspartate, where the solution of ammonium aspartate is prepared by any of the prior routes for production of aspartic acid. Specifically, stoichometric, substoichiometric, or suprastoichiometric amounts of one or more alkali compounds relative to the molar amounts of ammonium aspartate, either diammonium or monoammonium, may be added. The solutions are then dried by any method, preferably at a temperature of from 80 to 140° C., more preferably oven-dried at 120° C., to form the partial sodium salt of aspartate and aspartic acid, although residual ammonium aspartate may also be present. Drying could also be conducted by spray drying, lyophilization, vacuum methods or forced air. The drying can be halted at a time before polymerization of the comonomers begins. However, it is also possible to continue the drying step after the comonomers are formed to proceed with the copolymerization thereof, as discussed below, in situ.

During the drying step, the ammonia is largely released to the atmosphere, which ammonia gas may be scrubbed by passage through an acidified, cool-water trap. The ammonium aspartate thus reverts to the aspartic acid form. The sodium hydroxide acts to neutralize some of the aspartic acid upon drying. The sodium ion, having no significant vapor pressure, remains in the comonomeric salt composition of the present invention in the form of monosodium aspartate.

If the drying step is accomplished with heating in vacuo, by lyophilization, or with heating in an inert, oxygen-depleted atmosphere such as nitrogen gas, the resultant comonomeric salt of the present invention is a colorless, clear, glassy solid that may be obtained in various forms ranging from a solid puck to glassy particles to shards to powders.

Another preferred method of preparation of the comonomeric salts of the present invention is to mix stoichiometric, substoichiometric, or suprastoichiometric solutions of sodium aspartate with a solution of ammonium aspartate. For example dry or powdered aspartic acid may be solubilized by titration with a minimal amount of NaOH, just sufficient to render the aspartic acid into solution. Alternatively, the NaOH may be added in an excess, for example sufficient to provide two sodium ions per molecule of aspartic acid. Next, the two solutions are mixed, with addition of enough of one with the other to provide a combined solution containing the targeted molar ratio of ammonium versus sodium aspartate, in either case either the di- or monoammonium or di- or monosodium salts. The drying is then conducted as described above or by any other conventional means, leaving the resulting comonomer preparation of the present invention.

In any of the above methods the amounts of the aspartic acid and aspartate salts used are provided to reflect the desired ratio of amide and imide units in the eventual copolymer. The desired ratio may be selected based on the properties desired, e.g., a higher ratio of amide (aspartate) units in the copolymer will provide it greater solubility. Thus, e.g., a molar ratio of from 1:10 to 10:1, more preferably 1:4 to 4:1, particularly about 1:1, may be used.

The amide-generating or imide-generating monomers are not limited to ones having sodium and ammonium cations, respectively; other cations may be used in a manner analogous to that described above. As the amide-generating cations may be used those which form aspartate salts wherein the cation is non-volatile or not heat decomposable under the conditions for drying to the comonomer mixture. Preferred, therefore, are cations which exhibit no significant vapor pressure at 120° C. Representative examples include any metallic cation, such as alkali metal, alkaline earth metals or transition metals. Preferably the cations are alkali or alkaline earth metals, particularly Na, Mg, K, Ca, Rb, Sr, Cs and Ba, with sodium, magnesium, potassium and calcium, particularly sodium, being preferred alkali metals and alkaline earth metals. As the imide-generating cations may be used those which form aspartate salts which are volatile or heat decomposable under the conditions for drying to the comonomer mixture. Preferred, therefore, are cations that volatilize or are otherwise dissipated at 120° C. Representative examples include ammonium and other amines which provide counterions to aspartate carboxylic groups in solution, e.g., ethanolamine, propanolamine and monoaminobutane.

Comonomers in addition to the amide-generating and imide-generating aspartates may be used in the preparation of comonomer compositions for the production of imide-containing polyamino acids, and analogous methods to those described above using such other monomers are included in the invention. Use of such additional comonomers results in terpolymers or higher polymers. These further comonomers may be selected from among any comonomers which copolymerize and do not interfere with formation of the amide/imide copolymer units. Many useful comonomers are conventionally known and are included here, for example, other amino acids, e.g., any natural or modified amino acids as long as they contain at least one amino group and at least one carboxylic group free for polymerization and salts thereof.

The amount of the additional comonomer used is preferably in the range of 10 to 50% weight based on the total weight of the amide- and imide-generating comonomers.

An example of an additional comonomer is monosodium glutamate. Monosodium glutamate in dry form or as a solution may be added to a solution of ammonium aspartate, mixed to make a combined solution, then dried by any conventional means to produce a dried comonomer composition of aspartic acid and monosodium glutamate. The composition may also contain sodium aspartate, glutamic acid, or a combination of these comonomers.

Another preferred comonomer is lysine. Lysine, most preferably as the free base, and preferably having few or no counterions, such as chloride, associated with the amine groups of lysine, may be added in dry form or as a solution to a solution of ammonium aspartate, mixed to make a combined solution, then dried by any conventional means to produce a dried comonomer composition of aspartic acid and lysine. The composition may also contain sodium aspartate, glutamic acid, sodium glutamate, or a combination of these comonomers. Lysine may also be added as the chloride salt, lysine-HCl, but this is not particularly preferred, as the chloride may form counterions with free amino groups of the amino acids upon drying, blocking them from participating in the thermal polycondensation reaction to form the ultimate products, the imide-containing polyamino acids.

Lysine in the free-base form, which is prepared commercially as the zwitterion, when incorporated into the comonomer composition of the present invention, acts to extend the molecular size of the imide-containing polyamino acid products, presumably through chain-extension and crosslinking. Similarly, other diamino or polyamino monomeric coreactants may be used for this purpose. For example, ornithine may be used, as may aminocaproic acid, diaminohexane, diaminobutane and diaminopentane.

In all cases, the L-, D-, or mixed L-,D-isomers of the monomeric amino acids and other comonomers may be used.

In a separate embodiment for providing a comonomer mixture useful for obtaining imide-containing polyamino acids, sodium bicarbonate or other carbonate ion-providing compounds can be used. The water of condensation creates a vapor phase during the polymerization of aspartic acid. In the presence of sodium bicarbonate, bicarbonate anion can enter a transitory aqueous state, with sodium cation also solubilized momentarily. The bicarbonate decomposes in the presence of heat and water vapor to release $CO_2$ and water, further stirring the admixture through gaseous emission. The sodium can become a counterion to some of the aspartic residues in the form of monosodium aspartate, thus generating an intimate mixture of aspartic acid and monosodium aspartate comonomers. Upon thermal polymerization, this intimate mixture converts to the copolymer of aspartate and succinimide as further discussed below.

Manufacture of the imide-containing Polyamino Acids. The novel polymeric molecules of the present invention may be produced via methods analogous to those described in the prior art for manufacture, including commercial manufacture, of the homopolymers, polysuccinimide and polyaspartate, except of course using the comonomer compositions according to the invention. Accordingly, the molecules of the present invention may be manufactured by the approaches exemplified in Table 3, which includes relevant prior art references, incorporated herein in their entirety by reference. In one preferred embodiment, the comonomer mixture is heated by a thermal polycondensation method. Although the polymerization time and temperature will depend on the comonomer mixture used and the result desired, the polymerization can preferably be conducted at a temperature of from 140 to 350° C., more preferably 160 to 280° C., particularly 200 to 240° C., for preferably 1 minute to 72 hours, more preferably 5 minutes to 8 hours, to form the copolymers. In one embodiment of the preparation, a thin film evaporator may be used to provide a short time (e.g., as little as 5 minutes) for complete conversion of the monomers to the polymer due to the efficiency of heat exchange and removal of water of condensation.

The copolymers may be formed in a large range of molecular weights. In one embodiment, the copolymers may exhibit a gel permeation molecular weight of from 300 to 5,000 daltons, particularly 500 to 3,000 daltons. A higher ratio of succinimide units will generally result in a higher molecular weight copolymer. In other embodiments the copolymer may be polymerized to an extent to provide a molecular weight of 100,000 or higher. The molecular weight of the copolymer may be increased by including a polyamine (including diamines) as an additional comonomer; see the description regarding comonomers above. Suitable diamines and polyamines include aliphatic diamine, arylaliphatic diamines, as will as triamino, tetramino and polyamino compounds, such as polyoxyalkylene triamine, polyoxyalkylene diamine, triethylene tetraamine and tetraethylene pentamine. Such polyoxyalkylene amines are available, for example, as JEFFAMINES® from Huntsman Specialty Chemicals and as STARBURST® dendrimers from Dendritech, Inc. The JEFFAMINES® typically contain ethylene and/or propylene oxide units and have molecular weights ranging from 600 to 5000. Preferred polyamines are diaminopropane, diaminobutane, diaminopentane, diaminohexane, diaminoheptane, diaminoctane, ornithine, ornithine methyl ester, lysine, lysine methyl ester, spermine and spermidine. Particularly preferred diamines include diaminobutane, diaminopropane, diaminohexane and lysine methyl ester.

Typically, the polyamine is incorporated in a monomer mixture of polyamine and monosodium aspartate in an amount of 1 to 50 mole %, preferably 5 to 15 mole %, based on the total moles of polyamine and salt of aspartic acid in the monomer mixture. By including a polyamine in the monomer mixture it is possible to increase the molecular weight of the resulting poly(aspartate,succinimide) to 100,000 daltons and higher as measured by gel permeation.

In another embodiment, the present method may be carried out by polymerizing the comonomer mixture of the invention in the presence of a preformed polyaspartate. The preformed polyaspartate may be that prepared by a process analogous to that described in U.S. Pat. No. 5,981,691 or that prepared by some other conventional polymerization of aspartic acid or aspartates followed by hydrolysis. Typically, the preformed polyaspartate will have a gel permeation molecular weight of 1000 to 100,000, preferably 2000 to 30,000 daltons. The preformed polyaspartate is usually included in the polymerization in an amount of 25 to 95 mole %, preferably 50 to 90 mole %, based on the total moles of residues (monomer units) of the copolymer.

By the use of preformed polyaspartates or by other methods, copolymers according to the invention can be provided having at least a partially block copolymer structure. Additionally, graft copolymers can be provided according to known methods.

The copolymers of the invention can exhibit a linear structure or branched structure, including three-dimensional structuring. Crosslinking of the copolymers according to known methods can also be conducted. Also, a variety of terminal groups known in the art can be provided on the copolymers.

TABLE 3

Some Useful Thermal Manufacturing Processes For the Polymers Of the Present Invention, Including Prior Art References Related To Polyaspartates And Related Materials

| Thermal Manufacturing Processes | Patent Number | Year | Authors |
| --- | --- | --- | --- |
| Fluidized bed reactor (Littleford) | US 5057597 | 1991 | Koskan, L. P. |
| | WO 98/34976 | 1998 | Martin, D. A. |
| | US 5830985 | 1998 | Kroner, M. et al. |
| Kneading reactor, continuous | US 5610255 | 1997 | Groth, T. et al. |
| Microwave Reactor | US 4696981 | 1987 | Harada, K. et al. |
| Rapidly mixed coreactants in continuous reactors including: delay tubes high viscosity reactors (screw, List) Driers stirred tank cascades thin layer evaporators multi-phase spiral tubes | US 5594077 | 1997 | Groth, T. et al. |
| | US 5919894 | 1999 | Schubart, R. |
| Mixed coreactants in noncontinuous or continuous reactors including: kneading machines paddle driers screw machines belt driers roller driers | US 5371180 | 1997 | Groth, T. et al. |
| Tray driers (Wyssmont, Krauss Maffe) | US 5319145 | 1994 | Paik, Y. H. et al. |
| | US 5401428 | 1995 | Kalota, D. et al. |
| | WO 98/34976 | 1998 | Martin, D. A. |
| Rotary drier, Plate drier | US 5315010 | 1994 | Koskan, L. P. et al. |

Uses of the Imide-containing Polyamino Acids. The novel molecules of the present invention may be used in a manner analogous to that described in the prior art for possible uses of polysuccinimides and polyaspartates, including described commercial uses. Accordingly, the molecules of the present invention, i.e., including the described copolymers of aspartate and succinimide (i.e., the imide-containing polyamino acids) and the derivatives thereof discussed below, may be used as summarized in Table 4, which includes the relevant prior art references, incorporated herein in their entirety by reference.

TABLE 4

Uses of the Polymers of the Present Invention, Including Prior Art References to Uses of Polyaspartates and Related Materials.

| Use | Patent Number | Year | Authors |
| --- | --- | --- | --- |
| antifreezes antiscalants | US 5942150 | 1999 | Heuer, L. et al. |
| boiler water | US 5658464 | 1997 | Hann, W. M. et al. |
| cooling water | US 4534881 | 1985 | Sikes, C. S. and A. P. Wheeler |
| | US 5658464 | 1997 | Hann, W. M. et al. |
| desalinators | US 5548036 | 1996 | Kroner, M. et al. |
| fruit/sugar extraction | US 5939522 | 1999 | Mazo, G. Y. et al. |
| oilfield | EP 0 980 883 A1 | 2000 | Oda, Y. |
| | US 6022401 | 2000 | Tang, J. et al. |
| reverse osmosis membranes | WO 98/22205 A1 | 1998 | Groeschl, A. et al. |
| | US 6001956 | 1999 | Wood, L. L. and G. J. Calton |
| antistatics | US 5502251 | 1996 | Pohmer, K. et al. |
| | JP 08041445 A2 | 1996 | Tamaya, H. et al. |
| adhesives | US 5939522 | 1999 | Mazo, G. Y. et al. |
| bioabsorbable medical devices biological coatings | US 5397816 | 1995 | Reilly, E. P. et al. |
| antiproteolytic, | US 6022860 | 2000 | Engel, J. et al. |
| antihydrolytic | US 5834273 | 1998 | Futatsugi, M. and Kenji Gushi |
| cationic toxin suppressants | US 5498410 | 1996 | Gleich, G. J. |
| cell and tissue encapsulation | US 5573934 | 1996 | Hubbell, J. A. et al. |
| cellular adhesion inhibitors | US 5573934 | 1996 | Hubbell, J. A. et al. |
| cellular adhesion promoters | US 5470843 | 1995 | Stahl, W. et al. |
| | US 5395619 | 1995 | Zalipsky, S. et al. |
| coatings for food materials | US 5175285 | 1992 | Lehmann, K. et al. |

TABLE 4-continued

Uses of the Polymers of the Present Invention, Including Prior Art
References to Uses of Polyaspartates and Related Materials.

| Use | Patent Number | Year | Authors |
|---|---|---|---|
| immunosuppressants | US 5693514 | 1997 | Dorian, R. E. and K. C. Cochrum |
| pharmaceutical carriers | US 5578323 | 1996 | Milstein, S. J. and M. L. Kantor |
| blood plasma expanders | DE 2032470 | 1971 | Neri, P. et al. |
| botanical additives | | | |
| Herbicide absorption enhancers | US 5635447 | 1997 | Sanders, J. L. |
| Plant growth enhancers | US 5783523 | 1998 | Koskan, L. P. et al. |
| | US 5935909 | 1999 | Sanders, J. L. |
| Plant growth factors | US 6022860 | 2000 | Engel, J. et al. |
| Plant freshness preservatives | US 5580840 | 1996 | Harms, D. J. and A. R. Y. Meah |
| carriers of therapeutic agents | US 5904936 | 1999 | Huille, S. et al. |
| chelants, sequestrants | EP 0 826 716 A2 | 1998 | Nakato, T. and M. Tomida |
| | US 5936121 | 1999 | Gelosa, D. et al. |
| | EP 0 980 883 A1 | 2000 | Oda, Y. |
| chromatographic agents | US 4517241 | 1985 | Alpert, A. J. |
| conditioners | US 5925728 | 1999 | Kim, S. et al. |
| controlled release | | | |
| biocides | US 5904936 | 1999 | Huille, S. et al. |
| drugs | US 5904936 | 1999 | Huille, S. et al. |
| | US 6022860 | 2000 | Engel, J. et al. |
| flavors | US 5540927 | 1996 | Jason, M. E. and D. J. Kalota |
| fragrances | US 5556835 | 1996 | Inaoka, T. et al. |
| plant growth factors | US 5904936 | 1999 | Huille, S. et al. |
| corrosion inhibitors | JP 11350172 A | 1999 | Shokubai, N. |
| | EP 0 980 883 A1 | 2000 | Oda, Y. |
| | US 6022401 | 2000 | Tang, J. et al. |
| cosmetics | US 4363797 | 1982 | Jacquet, B. et al. |
| | US 4735797 | 1988 | Grollier, J. and C. Fourcadier |
| detergents and cleansers | | | |
| antiredeposition agents | US 5962400 | 1999 | Thomaides, J. S. et al. |
| builders | US 6001798 | 1999 | Baur, R. et al. |
| | US 5658872 | 1997 | Du Vosel, A. et al. |
| color protectants | US 6040288 | 2000 | Popoff, C. et al. |
| dye-transfer inhibitors | US 5639832 | 1997 | Kroner, M. et al. |
| fragrance retaining aids | US 6040288 | 2000 | Popoff, C. et al. |
| liquid laundry dispersants | JP 11092787 A | 1999 | Nippon Shokubai |
| powdered laundry dispersants | US 5266237 | 1993 | Freeman, M. B. et al. |
| | US H 1,514 | 1996 | Willman, K. and J. Vandermeer |
| | US 5770553 | 1998 | Kroner, M. et al. |
| soil release agents dispersants | US 5902782 | 1999 | Hall, R. G. and A. D. Willey |
| cement | US 5908885 | 1999 | Sikes, C. S. et al. |
| ceramic and | US 5328690 | 1994 | Sikes, C. S. |
| metal particles | US 5503771 | 1996 | Staley, J. T. et al. |
| coal | US 5548036 | 1996 | Kroner, M. et al. |
| drilling mud | US 5552514 | 1996 | Adler, D. E. et al. |
| inks | WO 97/43351 | 1997 | Krepski, et al. |
| milling | EP 0860 477 A1 | 1998 | Suau, J. M. et al. |
| pigments | US 5371180 | 1994 | Groth, T. et al. |
| | WO 97/43351 | 1997 | Krepski, L. R. et al. |
| | US 5902357 | 1999 | Riegels, M. et al. |
| dye-levelers | US 5902357 | 1999 | Riegels, M. et al. |
| emulsion stabilizers | US 5910564 | 1999 | Gruning, B. et al. |
| | US 6143817 | 2000 | Hallam, M. et. al. |
| fertilizers | US 4839461 | 1989 | Boehmke, G. |
| fiber treatment agents | | | |
| carpets | DE 196 35 061 A1 | 1998 | Groth, T. et al. |

TABLE 4-continued

Uses of the Polymers of the Present Invention, Including Prior Art
References to Uses of Polyaspartates and Related Materials.

| Use | Patent Number | Year | Authors |
|---|---|---|---|
| clothes | DE 196 35 061 A1 | 1998 | Groth, T. et al. |
| foaming agents | DE 196 35 061 A1 | 1998 | Groth, T. et al. |
| hair products | DE 197 20 771 | 1998 | Ferencz, A. et al. |
| flame and fire retardants | US 5502251 | 1996 | Pohmer, K. et al. |
| flocculents | WO 96/08523 | 1996 | Ross, R. J. et al. |
| foam inhibitors | US 5401428 | 1995 | Kalota, D. J. et al. |
| foam stabilizers | US 5910564 | 1999 | Gruning, B. et al. |
| fungicides | US 5874025 | 1999 | Hewer, L. et al. |
| gas hydrate inhibitors | WO 96/29502 | 1996 | Duncum, S. et al. |
| gelling materials | | | |
| agricultural uses | US 5981761 | 1999 | Chou, Y. et al. |
| fibers | US 6027804 | 2000 | Chou, Y. et al. |
| films | US 5997791 | 1999 | Chou, Y. et al. |
| food related uses | US 5981761 | 1999 | Chou, Y. et al. |
| sanitary articles | US 5773564 | 1998 | Sikes, C. S. |
| | US 5955549 | 1999 | Chang, J. et al. |
| water sealing agents | US 5981761 | 1999 | Chou, Y. et al. |
| hair curling agents, strengtheners | US 5961965 | 1999 | Kim, S. et al. |
| humectants | EP 0 826 716 A2 | 1998 | Nakato, T. and M. Tomida |
| industrial coatings | | | |
| binders | US 5597930 | 1997 | Wicks, D. A. et al. |
| removable coatings | US 5910532 | 1999 | Schmidt, D. L. and R. D. Mussell |
| smoothing, glossing agents | US 6013755 | 2000 | Primeaux, D. J. et al. |
| spreading, adhesion agents | US 6013755 | 2000 | Primeaux, D. J. et al. |
| insecticides enhancers | US 5646133 | 1997 | Sanders, J. L. |
| ion exchange resins | US 4517241 | 1985 | Alpert, A. J. |
| leather auxiliary compounds | US 5885474 | 1999 | Reiners, J. et al. |
| lipid lowering agents | US 5516758 | 1996 | Stevens, K. R. and W. V. Taggart |
| lubricants | US 6015776 | 2000 | Harrison, J. J. and W. R. Ruhe |
| metal cleansing fluids | US 5443651 | 1995 | Kalota, D. J. and D. C. Silverman |
| metal working fluids | US 5401428 | 1995 | Kalota, D. J. et al. |
| | US 5616544 | 1997 | Kalota, D. J. et al. |
| microbiocides | US 5493004 | 1996 | Groth, T. et al. |
| molded materials | JP 10139880 A | 1998 | Mitsubishi |
| components | JP 10168326 A | 1998 | Mitsui Toatsu |
| odor control substances | US 5833972 | 1998 | Wood, L. L. and G. J. Calton |
| oil absorbents | US 5641847 | 1997 | Hozumi, Y. et al. |
| | US 5773564 | 1998 | Sikes, C. S. |
| paper products | | | |
| dewatering agents | US 5886095 | 1999 | Bayer, R. et al. |
| strength enhancers | US 5902862 | 1999 | Allen, A. J. |
| | US 6022449 | 2000 | Jansen, B. et al. |
| suspension agents | EP 0860 477 A1 | 1998 | Suau, J. M. et al. |
| shampoos and lotions | US 5686066 | 1997 | Harada, Y. et al. |
| | DE 197 20 771 | 1998 | Ferencz, A. et al. |
| surfactants | US 6040288 | 2000 | Popoff, C. et al. |
| tartar control | US 4866161 | 1989 | Sikes, C. S. and A. P. Wheeler |
| | US 5266305 | 1993 | Wood, L. L. and G. J. Calton |
| thickening agents | WO 95/35337 | 1995 | Ross, R. J. et al. |
| | US 5773564 | 1998 | Sikes, C. S. |
| tissue-engineering scaffolding | US 5654381 | 1997 | Hrkach, J. S. et al. |
| | US 5981467 | 1999 | Hogan, J. C. |
| viscosity modifiers | WO 98/34976 | 1998 | Martin, D. |
| | US 5804639 | 1998 | Schopwinkel, G. et al. |
| | US 5886137 | 1999 | Kroner, M. et al. |

Preferred but non-limiting uses of the copolymers or the below-discussed derivatives thereof include, use as: detergent, e.g., liquid or powdered, additives; cosmetic additives, such as softeners or emollients; hair conditioner or shampoo additives; dispersants in cementitious materials; active agents in coatings, crosslinkers or binders; antiscalants; corrosion inhibitors; adhesives; strengthener or binder agents for paper products; and gelling or thickening agents.

Derivatization. In addition to the uses as described above, the polyamino acids of the present invention preferably may be used in the synthesis of advanced derivatives. That is, advanced derivatives may be prepared via nucleophilic addition of nucleophilic group-containing compounds, such as amine or —OH group-containing compounds, to the imide residues of the imide-containing polyamino acids of the present invention. These pendant compounds become attached to the polymer backbone, for example, via amide bonds for the amine compounds or via ester bonds for the —OH group-containing compounds.

Preferably, the derivatization is accomplished in an aqueous solution of the imide-containing polyamino acids. Particularly preferred are aqueous solutions adjusted to the nucleophilic pH range. For example, a preferred pH range is 8 to 12. Particularly preferred is the pH range of 10 to 11. The derivatization can be conducted at a wide range of temperatures with 5 to 90° C., more preferably 20 to 60° C., particularly 30 to 50° C., being preferred. The amount of the succinimide units derivatized can vary from 1 to all of such units. Some nucleophilic add-ons may be reacted from an emulsion.

Although water is the preferred solvent, organic solvents may be used as well, particularly in the case in which the imide-containing polyamino acids are partially or completely insoluble in water. Preferred polar solvents in these cases are alcohols, particularly isopropanol. Preferred non-polar solvents are dimethyl formamide, dichloromethane, and particularly N-methyl-pyrrolidone. In some cases, miscible solutions of more than one solvent, including water, may be preferred for derivatization of particular imide-containing polyamino acids.

If the preferred nucleophile itself is not very water-soluble, it may be added as an emulsion to the solution of the imide-containing polyamino acid. For example, the hair-conditioning agent trimethylsilylamodimethicone, is such a water-insoluble nucleophile that may be added as an emulsion to the water-soluble, imide-containing polyamino acid.

Particularly preferred examples of amine compounds for making the derivatives include monoamino polyoxyalkylenes, monoamino siloxanes, monoamino phosphonates, monoamino sulfonates, ethanolamine, and other amino alcohols. These amine compounds may be at one imide residue per polymer molecule, at every imide residue per molecule, or at any other percentage of the imide residues per polymer molecule.

Similarly, amino acids in general also may be added to the imide-containing polymers of the present invention via nucleophilic addition. For example, preferred additional amino acids to be added via this approach include: leucine, to provide hydrophobic character; serine, to provide a pendant alcoholic group; dihydroxyphenylalanine, to provide catecholic character; phosphoserine, to provide a stronger anionic pendant group; alanine, to provide intermediate hydrophobicity, etc. Other amino acids can be added to extend the molecules, for example preferably aminocaproic acid and caprolactam. Thus, any and all amino acids may be added to the imide-containing polyamino acids via nucleophilic addition, for the purposes of adding functional group characteristics ranging from hydrophobic, to nonionic, to anionic, to cationic.

Another preferred embodiment of production of the advanced derivatives is to add OH-containing molecules to the imide residues of the imide-containing polyamino acids via nucleophilic addition under mildly alkaline aqueous conditions with or without mild heating. These pendant compounds become attached to the polymer backbone via ester linkages.

Preferred examples of the OH-containing compounds for addition to the polymer backbones include monomeric carbohydrates and disaccharides such as glucose, galactose, mannose, lactose, sucrose, and others. In addition, polysaccharides such as cellulose, starch, amylose, as well as their oligosaccharide fragments, may be reacted with the imide-containing polyamino acids.

In each preferred embodiment in which the succinimide residues are derivatized with added functional molecules, it is possible to derivatize all of the succinimide residues per molecule of the imide-containing polyamino acids. It is also possible to derivatize as few of the succinimide residues per polymer molecule as may be desired, or even less than 1 succinimide residue per molecule, on average. For example, it is possible to derivatize from 1% to 100% of the available succinimide residues in a solution of the imide-containing polyamino acids. Preferably, from 5% to 80% would be derivatized; more preferably from 10% to 60%; most preferably from 20% to 50%.

In addition, it is possible to add the nucleophile derivatizing molecules to a solution of the imide-containing polyamino acids; or alternatively, it is possible to add the imide-containing polyamino acids to a solution of the nucleophile derivatizing molecules. For example, if there is an excess of nucleophilic amines left free in solution due to a limitation of available succinimide residues for whatever reason, it is possible to add more of the imide-containing polyamino acid until all of the nucleophilic amines attach covalently to the polymer.

The derivatized copolymers are useful in a manner analogous to the copolymers, as described above, but exhibit the modified properties imparted by the added pendant groups.

BRIEF DESCRIPTION OF THE DRAWINGS

Various other features and attendant advantages of the present invention will be more fully appreciated as the same becomes better understood when considered in conjunction with the accompanying drawings wherein the figures depict the following.

The entire disclosure of all applications, patents and publications, cited above and below, are hereby incorporated by reference.

EXAMPLES

In the foregoing and in the following examples, all temperatures are set forth uncorrected in degrees Celsius.

Infrared Spectroscopy

Infrared spectra of the monomers, the comonomeric preparations, the homopolymers, and the copolymers were measured by use of an FTIR spectrophotometer (Perkin Elmer, model 1600). Samples were mixed in KBr and 13 mm, disc pellets were made at 9000 lbs. for 3 minutes by use of a die (Spectratech) and press (Carver, Inc.).

Molecular Weight

Molecular weights of polymers were determined by gel permeation. Standards were polyaspartates made in-house by solid-phase methods (Asp$_5$ through Asp$_{60}$) and commercial polyaspartates (up to 32,000 MW; low-angle, laser light scattering, Sigma Chemical) and polyglutamates (up to 80,000 MW; low-angle, laser light scattering, Sigma Chemical). A liquid chromatograph (Varian, model 5500) with a 7.5 mm×30 cm column (G 4000 PW, Phenomenex). The mobile phase was 0.01 M Tris, 0.1 M NaCl, pH 8.00, flow of 1 ml/min, UV detection at 235 nm.

Amino Acid Analysis

Confirmation of the composition of the imide-containing polyamino acids and their derivatives was determined by the PICOTAG protocol (Waters). A sample of 10 $\mu$l of a 1 $\mu$g/ml stock solution of the polymer was hydrolyzed in vacuo at 150° C. for 1 hour in the presence of HCl vapor to yield amine containing monomers. These were derivatized with phenylisothiocyanate and measured by reverse-phase liquid chromatography (Spectraphysics model 8800), 3.9 mm×15 cm column (Waters Division, Millipore, Inc.), acetonitrile gradient, UV detection at 254 mm, detection limit of 10 pmoles per residue.

Alkalimetric Titration of COOH Groups.

Figure 1:
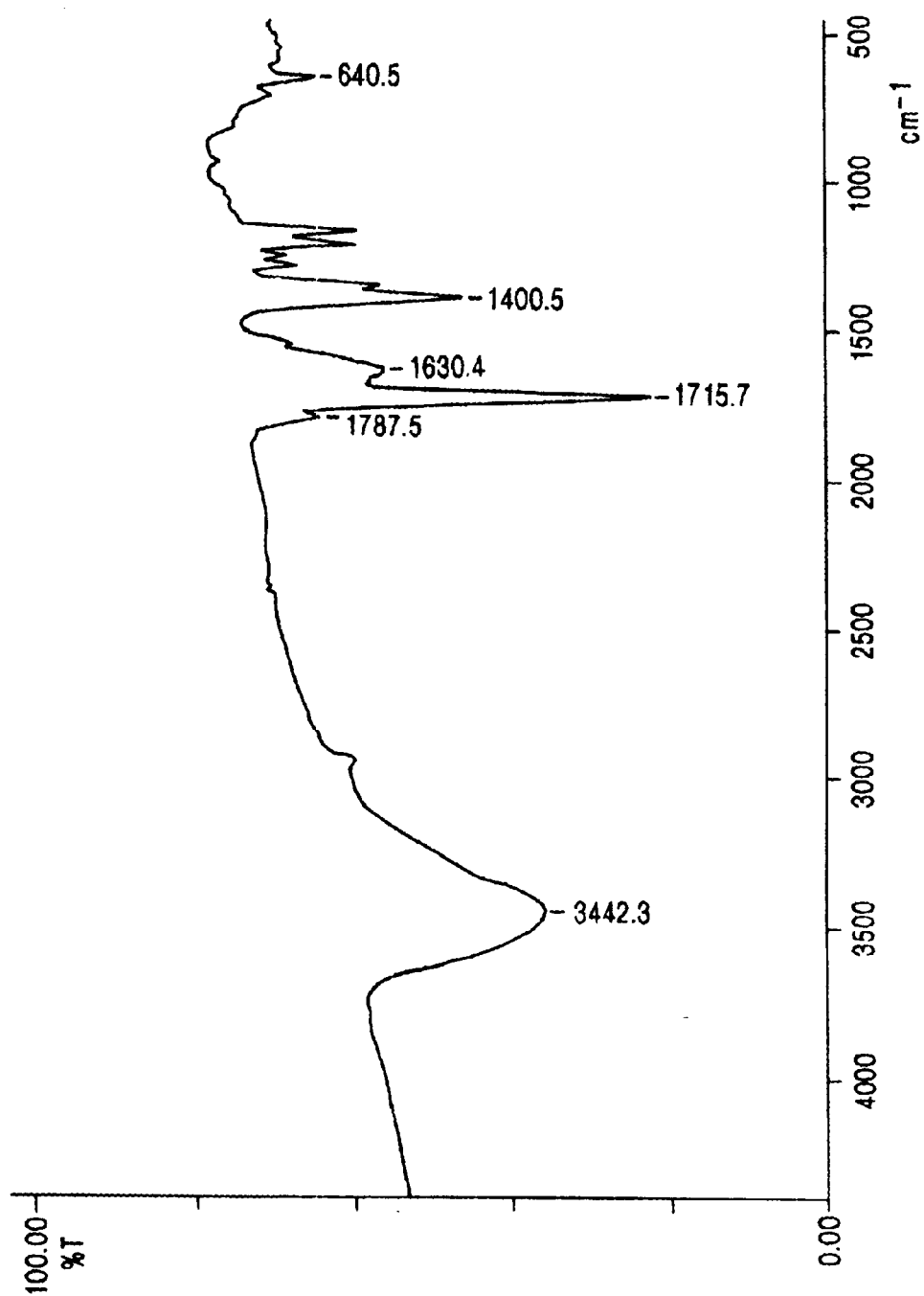
FIG. 1. Infrared spectrum of polysuccinimide. Note the characteristic imide peak at ~1716 $cm^{-1}$. This polysuccinimide was produced via thermal polymerization of aspartic acid at 220° C. for 8 hours, yielding a completely water-insoluble polymer of Mw~3000. Note the evidence of some degree of ring-opened structure as suggested by the amide peak at 1630 $cm^{-1}$, which is thought to signify branch points, each of which would terminate in carboxylic groups. The carboxylic groups are signaled by the peak at 1400 $cm^{-1}$.
Figure 2:
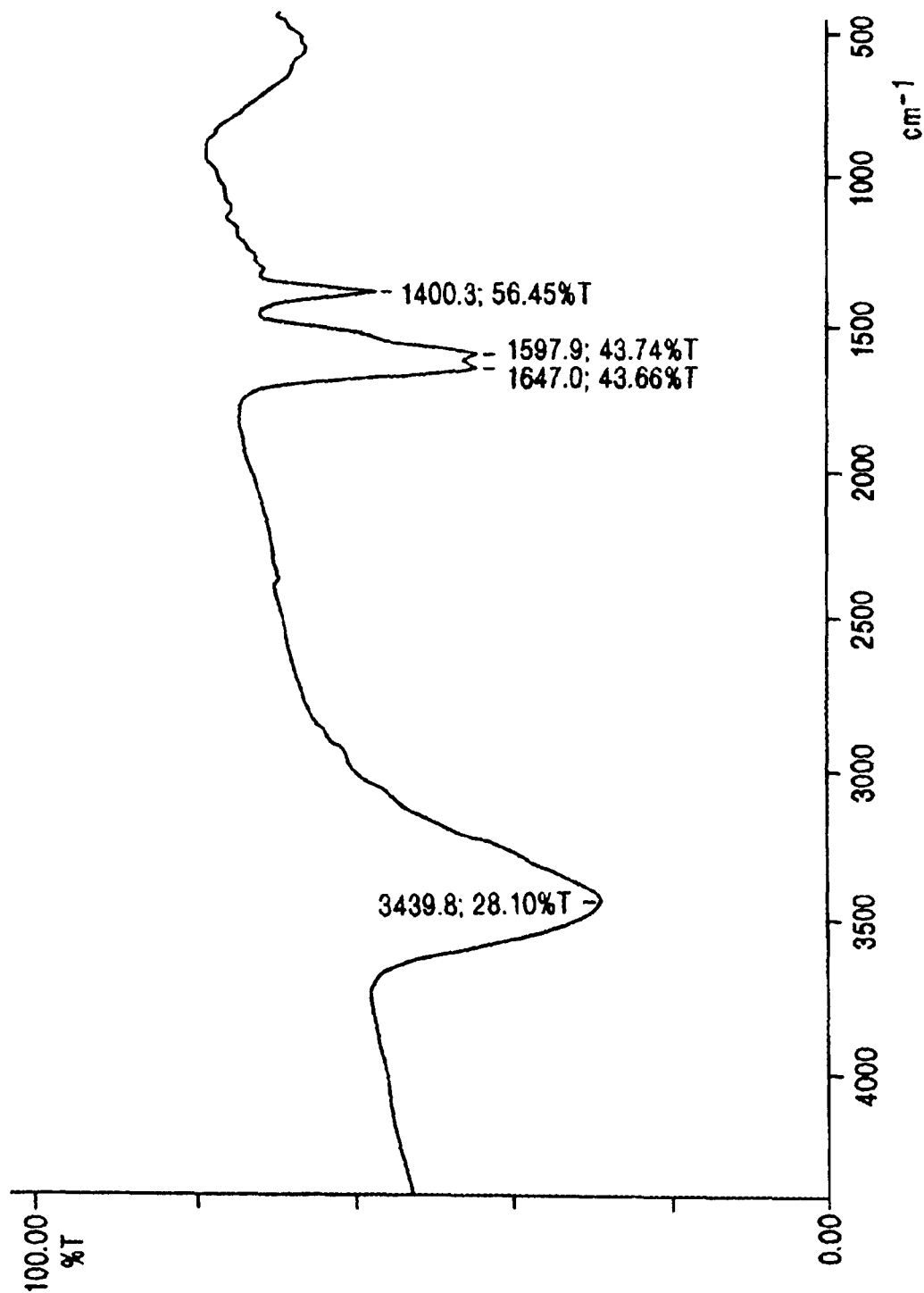
FIG. 2. Infrared spectrum of sodium polyaspartate, prepared by mild alkaline hydrolysis (succinimide ring-opening) of the polysuccinimide of FIG. 1. This polyaspartate was 11% by weight $Na^+$, determined by flame photometry. Note the characteristic amide doublet at ~1600 and 1650 $cm^{-1}$, as well as the prominent carboxylate signal at ~1400 $cm^{-1}$.
Figure 3:
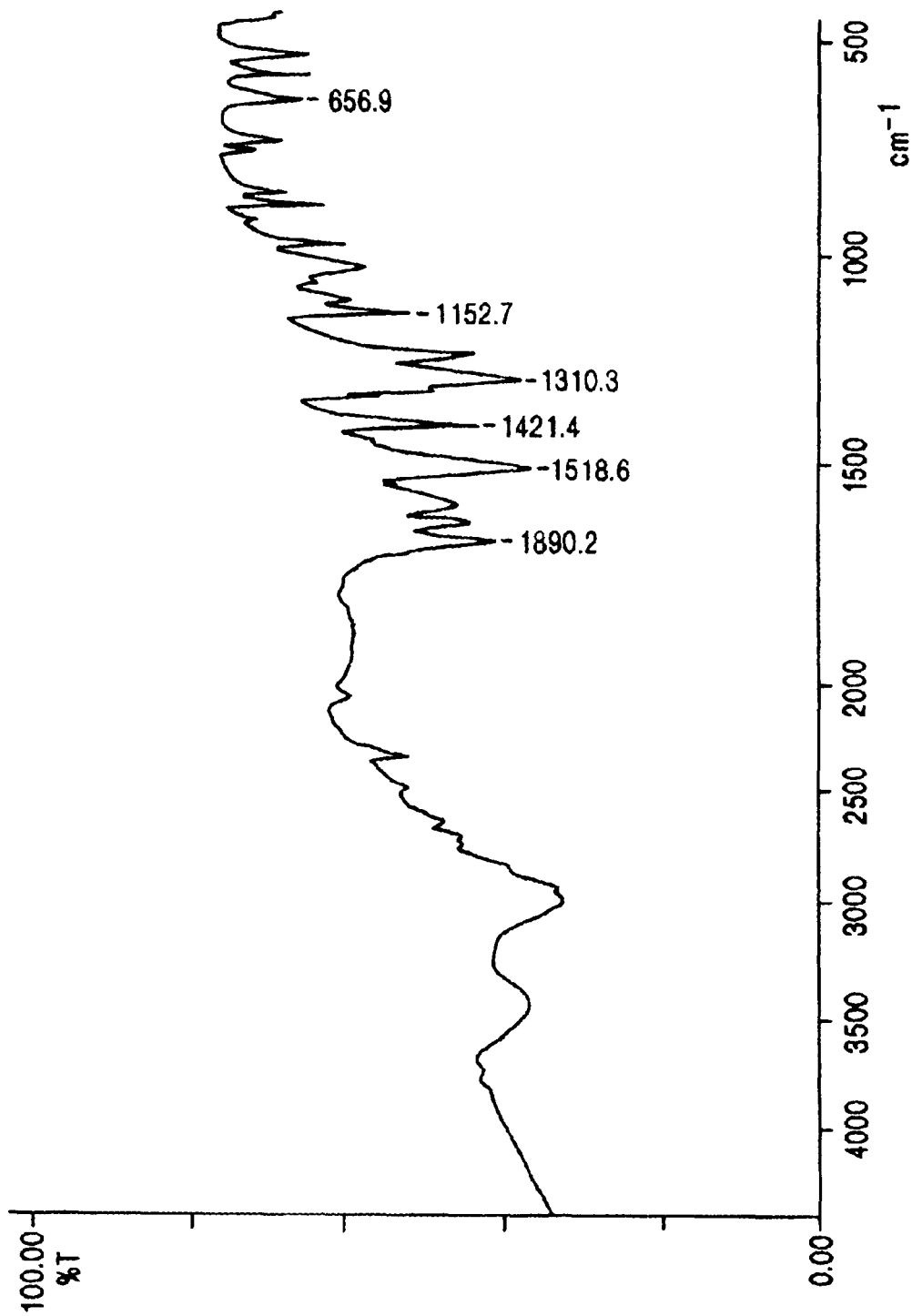
FIG. 3. Infrared spectrum of L-aspartic acid (zwitterion) prepared by acid precipitation of ammonium aspartate produced via immobilized enzymatic technology. Note the multiplicity of peaks in the "fingerprint" region between 500 and 1000 $cm^{-1}$.
Figure 4:
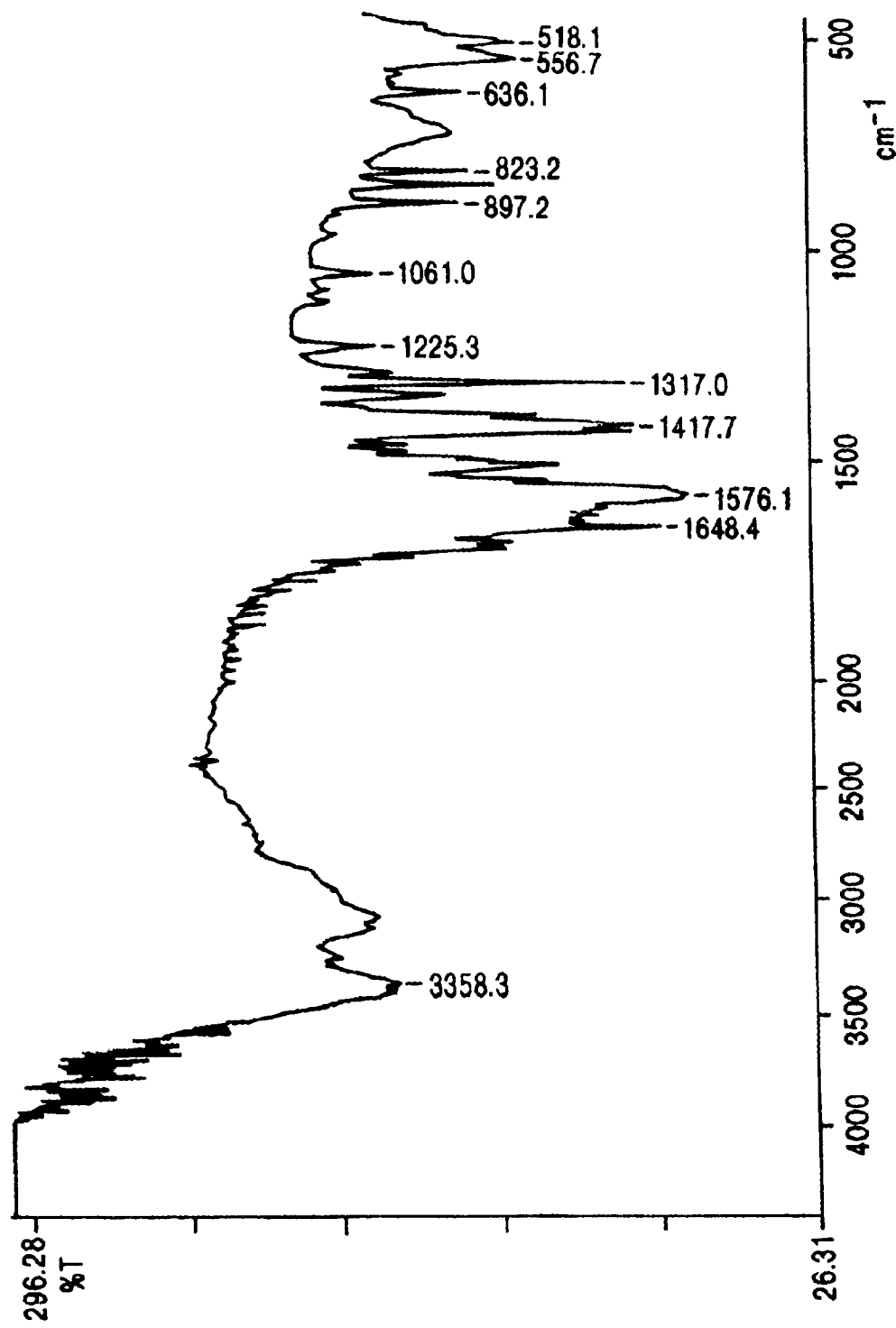
FIG. 4. Infrared spectrum of monosodium aspartate. Note the multiplicity of peaks in the "fingerprint" region between 500 and 1000 $cm^{-1}$.
Figure 5:
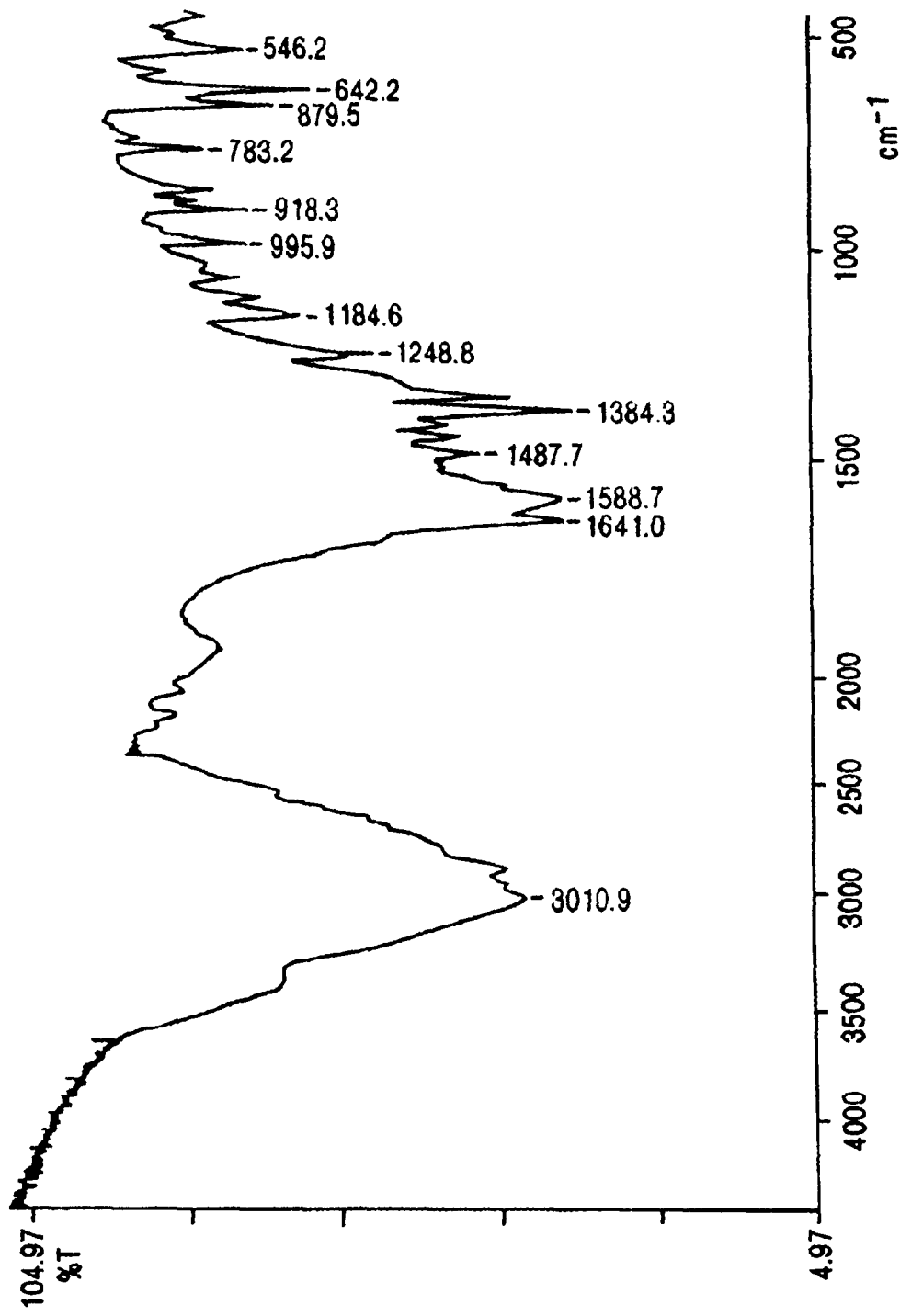
FIG. 5. Infrared spectrum of L-aspartic acid produced via drying in vacuo at 120° C. of a solution of monoammonium aspartate prepared by titration of L-aspartic acid (zwitterion) of FIG. 3 with ammonium hydroxide. Note the multiplicity of peaks in the "fingerprint" region between 500 and 1000 cm$^{-1}$ and the match between this spectrum and the spectrum of FIG. 3.
Figure 6:
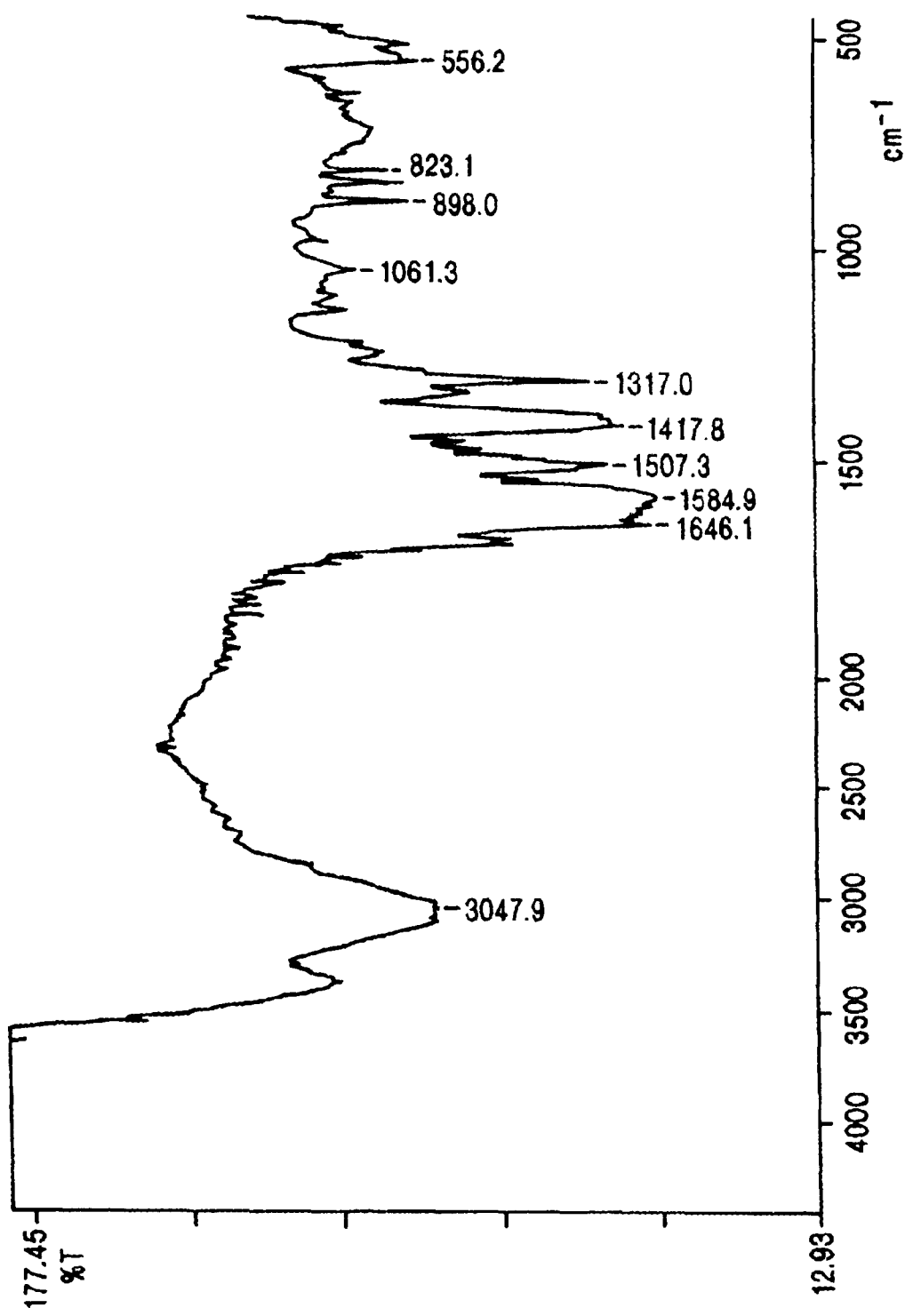
FIG. 6. Infrared spectrum of a lyophilized, comonomeric preparation of the partial sodium salt of the comonomers, aspartic acid (prepared from a solution of ammonium aspartate) and monosodium aspartate, present in a 1:1 molar ratio.

The relative proportions of aspartate residues and succinimide residues in the copolymers were also measured via quantitative titration of the carboxylic groups of the aspartate residues. Samples of approximately 100 mg were dissolved or dispersed (if not completely soluble) in 50 ml of water. The pH was adjusted to 2.50 by addition of 1 N HCl, then immediately autotitrated to an endpoint of 7.00 with 0.1 N NaOH by use of a computer assisted titrimeter (Fisher Scientific). Comparisons of theoretical versus actual number of titratable groups per unit weight of sample of the imide-containing copolymers were made. Control titrations of homopolymers of polyaspartate and polysuccinimide were used in the comparisons. The control polymers were made by thermal polycondensation of reagent grade L-aspartic acid (Sigma Chemical) at 220° C. for 8 hours. This treatment produced a homopolymer of polysuccinimide as evidenced in the IR spectrum of FIG. 1. Following the ring-opening treatment by mild alkaline hydrolysis, this polysuccinimide was converted to the corresponding sodium polyaspartate as evidenced in the IR spectrum of FIG. 2.

Example 1

Preparation of a comonomeric composition from a 1:1 equivalent solution of ammonium aspartate and monosodium aspartate, including air-drying at 120° C.

An amount of 6.65 g of aspartic acid (0.05 mole, MW 133, Sigma Chemical, L isomer) was slurried with magnetic stirring in 50 ml $H_2O$ in a 600 ml beaker. An equivalent amount of $NH_4OH$ (32 ml of a 1:10 dilution of concentrated ammonium hydroxide, 30% solution, 15.9 M) was added, converting the aspartic acid to monoammonium aspartate in solution. To this was added 8.65 g (0.05 mole) of monosodium aspartate (monohydrate, Sigma Chemical), which readily dissolved. The solution was oven-dried in air at 120° C. overnight to form a solid, light yellow but clear, glassy puck.

The beaker containing the puck was rapidly cooled by partial immersion and rotation in a methanol bath to which dry ice was added (temperature approaching −30° C.), leading to a clean separation of the puck from the glass. The puck was next fractured manually via mortar and pestle to produce a granular, glassy product of a comonomeric composition of sodium aspartate and aspartic acid.

The yield was 15.5 g. This was approximately 1.3% greater than theoretical (15.3 g) based on the starting amounts of aspartic acid and monosodium aspartate. The small excess was attributed to residual water and ammonium ion that remained after the drying step.

Example 2

Preparation of a comonomeric composition from a 1:1 equivalent solution of ammonium aspartate and monosodium aspartate, including vacuum-drying at 120° C.

The procedures of example 1 were followed except that the drying step was accomplished in vacuo at a pressure of 50 to 100 mm Hg by use of a vacuum oven set at 120° C. (VWR Scientific, model 1430).

Figure 7:
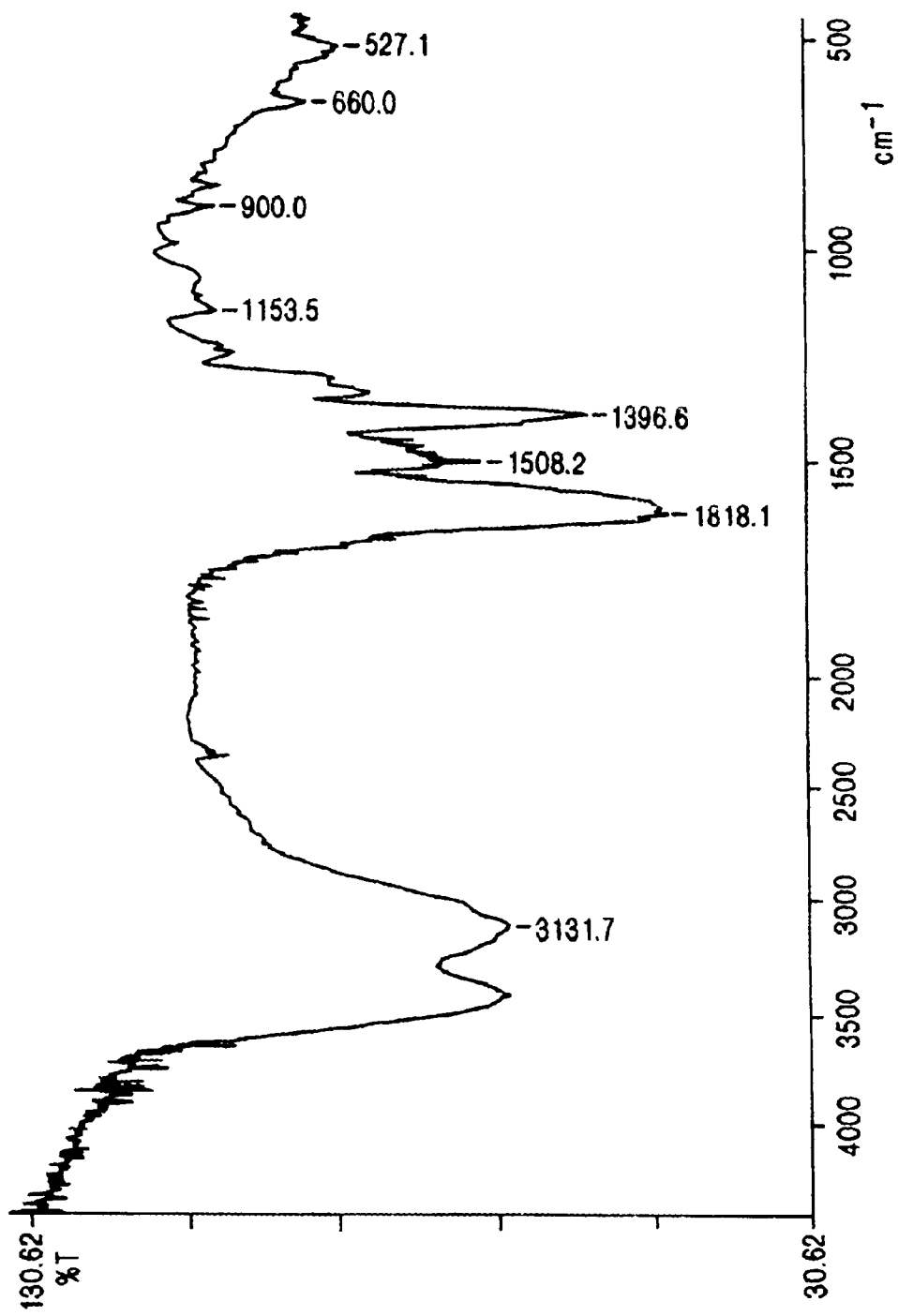
FIG. 7. Infrared spectrum of a vacuum-oven-dried (120° C., 50 mm Hg) comonomeric preparation of the present invention: partial sodium salt of the comonomers, aspartic acid (prepared from a solution of ammonium aspartate) and monosodium aspartate, present in the salt in a 1:1 molar ratio. Note the peaks in the "fingerprint" region between 500 and 1000 cm$^{-1}$, but also the amide-like peak around 1600 cm$^{-1}$ and the carboxylate peak around 1400 cm$^{-1}$. Notice particularly the differences between this spectrum, the spectrum of FIG. 6, and the spectra of L-aspartic acid (FIGS. 3 and 5) and monosodium aspartate (FIG. 4).

The resulting comonomeric composition of sodium aspartate and aspartic acid was obtained in a yield of 15.37 g, which was very close to theoretical (15.3 g), the difference again attributed to residual water and ammonium ion. In this case, the comonomeric product was colorless, clear, and glassy (for an infrared spectrum, see FIG. 7).

Example 3

Preparation of a comonomeric composition from a 1:1 equivalent solution of ammonium aspartate and monosodium aspartate by addition of 0.5 equivalents of NaOH to a solution of ammonium aspartate, followed by vacuum-drying at 120° C.

An amount of 6.65 g of aspartic acid (0.05 mole, MW 133, Sigma Chemical, L isomer) was slurried with magnetic stirring in 50 ml $H_2O$ in a 600 ml beaker. An equivalent amount of $NH_4OH$ (32 ml of a 1:10 dilution of concentrated ammonium hydroxide, 30% solution, 15.9 M) was added, converting the aspartic acid to monoammonium aspartate in solution. To this was added 0.025 mole of NaOH as 2.5 ml of 10 N NaOH. The solution was vacuum-dried (50 to 100 mm HG) at 120° C. overnight to form a solid, clear, glassy puck.

The puck was treated as described in example 1 to produce a solid, glassy, fractured, granular comonomeric composition.

Example 4

Preparation of a comonomeric composition from a 1:1 equivalent solution of ammonium aspartate and monosodium aspartate by addition of 0.5 equivalents of NaOH to a solution of ammonium aspartate, prepared from maleic acid (anhydride) and ammonia, followed by vacuum-drying at 120° C.

In a 250 ml reagent bottle, an amount of 69 ml (0.11 mole) of a 10% solution of concentrated ammonium hydroxide (15.9 M) was slowly added with smooth stirring to 9.8 g (0.1 mole) of maleic anhydride in 18 ml (1 mole) of water at 60° C. The bottle was capped and the solution allowed to react for 2 hours. The anhydride converted to maleic acid in the presence of the water, and the ammonia added across the double bond of maleic acid to form aspartic acid.

Next, the solution was poured into a 600 ml beaker, then neutralized with 0.05 mole of NaOH added as 5 ml of 10 N NaOH to yield a solution of aspartic acid and sodium aspartate in a 1:1 molar ratio, with a small excess of ammonia. Upon vacuum-drying (50 to 100 mm Hg) at 120° C., the ammonia was released, leaving the solid, glassy puck of the dried composition of the comonomers of the present invention.

The puck was treated as described in example 1 to produce a solid, glassy, fractured, granular comonomeric composition.

Example 5

Preparation of a comonomeric composition from a 1:1:1 equivalent solution of ammonium aspartate, monosodium aspartate, and lysine, including air-drying at 120° C.

An amount of 3.99 g of aspartic acid (0.03 mole) was slurried with magnetic stirring in 30 ml $H_2O$ in a 100 ml beaker. An equivalent amount of $NH_4OH$ was added, converting the aspartic acid to monoammonium aspartate in solution. To this was added 5.19 g (0.03 mole) of monosodium aspartate monohydrate, which readily dissolved. Next, 4.926 of L-lysine monohydrate (free base, Mw 164.2) was added, which also dissolved completely. The solution was oven-dried in air at 120° C. overnight to form a solid, light yellow but clear, glassy puck.

The puck was treated as described in example 1 to produce a solid, glassy, fractured, granular comonomeric composition.

Example 6

Preparation of a comonomeric composition from a 1:1:0.6 equivalent solution of ammonium aspartate, monosodium aspartate, and lysine, including air-drying at 120° C.

The procedure of example 5 was followed except that the lysine was added as 2.956 g (0.018 mole). This produced a solid comonomeric composition having an equivalent ratio of 1:1:0.6 of aspartate:aspartic acid (from drying of soluble ammonium aspartate):lysine.

Example 7

Preparation of a comonomeric composition from a 1:1:0.5 equivalent solution of ammonium aspartate, monosodium aspartate, and lysine, including air-drying at 120° C.

An amount of 6.65 g of aspartic acid (0.05 mole) was slurried with magnetic stirring in 50 ml $H_2O$ in a 250 ml beaker. An equivalent amount of $NH_4OH$ was added, converting the aspartic acid to monoammonium aspartate in solution. To this was added 8.65 g (0.05 mole) of monosodium aspartate monohydrate, which readily dissolved. Next, 3.65 g of L-lysine monohydrate (free base, Mw 164.2, 0.025 mole) was added, which also dissolved completely. The solution was oven-dried in air at 120° C. overnight to form a solid, light yellow but clear, glassy puck, followed by production of a solid, granular, glassy, pale yellowish comonomeric composition as above. In this case, the molar ratio of aspartate:aspartic acid (dried from soluble ammonium aspartate):lysine was 1:1:0.5.

Example 8

Preparation of a comonomeric composition from a 1:1:0.5 equivalent solution of ammonium aspartate, monosodium aspartate, and lysine, including lyophilization to form the intimate comonomeric composition as a dried salt.

The procedure of example 7 was followed, except that the solution of the comonomers was dried by lyophilization to produce a powdery, clear, glassy solid, comonomeric composition.

Example 9

Preparation of a comonomeric composition from a 1:1 solution of aspartic acid and lysine, including air-drying at 120° C.

A amount of 6.65 g of aspartic acid (0.05 mole) was slurried in 50 ml of water as in example 7. To this was added 8.21 g (0.05 mole) of lysine free base, which itself acted to neutralize the aspartic acid, bringing it into solution, without the need for addition of ammonium hydroxide. This solution was dried at 120° C. in air, producing a clear, yellowish, glassy puck. This then was treated as above to yield a solid, granular, glassy comonomeric composition of aspartate and lysine. As shown below, e.g., see Example 21, polymerization of such comonomeric composition resulted in a product which was not water-soluble.

Example 10

Thermal polymerization of the 1:1 equivalent comonomeric composition prepared from the solution of monosodium aspartate and monoammonium aspartate to produce a copolymer of sodium aspartate and succinimide by thermal treatment at 220° C.

The comonomeric composition of example 1 was prepared as follows. An amount of 6.65 g of aspartic acid (0.05 mole, MW 133, Sigma Chemical, L isomer) was slurried with magnetic stirring in 50 ml $H_2O$ in a 600 ml beaker. An equivalent amount of $NH_4OH$ (32 ml of a 1:10 dilution of concentrated ammonium hydroxide, 30% solution, 15.9 M) was added, converting the aspartic acid to monoammonium aspartate in solution. To this was added 8.65 g (0.05 mole) of monosodium aspartate (monohydrate, Sigma Chemical), which readily dissolved. The solution was oven-dried at 120° C. overnight to form a comonomeric composition in the form of a solid, clear, glassy puck.

The material was next thermally polymerized at 220° C. for 2 hours in a vacuum oven at a pressure of 50 mm of Hg. During this treatment, the glassy puck of the intimate salt of aspartic acid and monosodium aspartate initially boiled for a few moments, driving off residual water of solution, then as the temperature of the material equilibrated with the ambient temperature of the oven, the polymerization began. This was accompanied by a rising of the mass as the water of condensation evolved. The material, being ionic and moist at first, was sticky and was carried upward as the water was driven off. The material can be briefly retrieved from the oven and manually pushed downward into the beaker, keeping track of the time at temperature, or the vacuum may be released from time to time to promote the collapse of the rising mass.

The material hardens after approximately 1 hour of reaction, no longer being moist, at which point, it can be packed manually into the reaction vessel. Or it may be left as is, in a somewhat foamed condition, allowing the reaction to proceed to completion over the next hour at 220° C.

Figure 8:
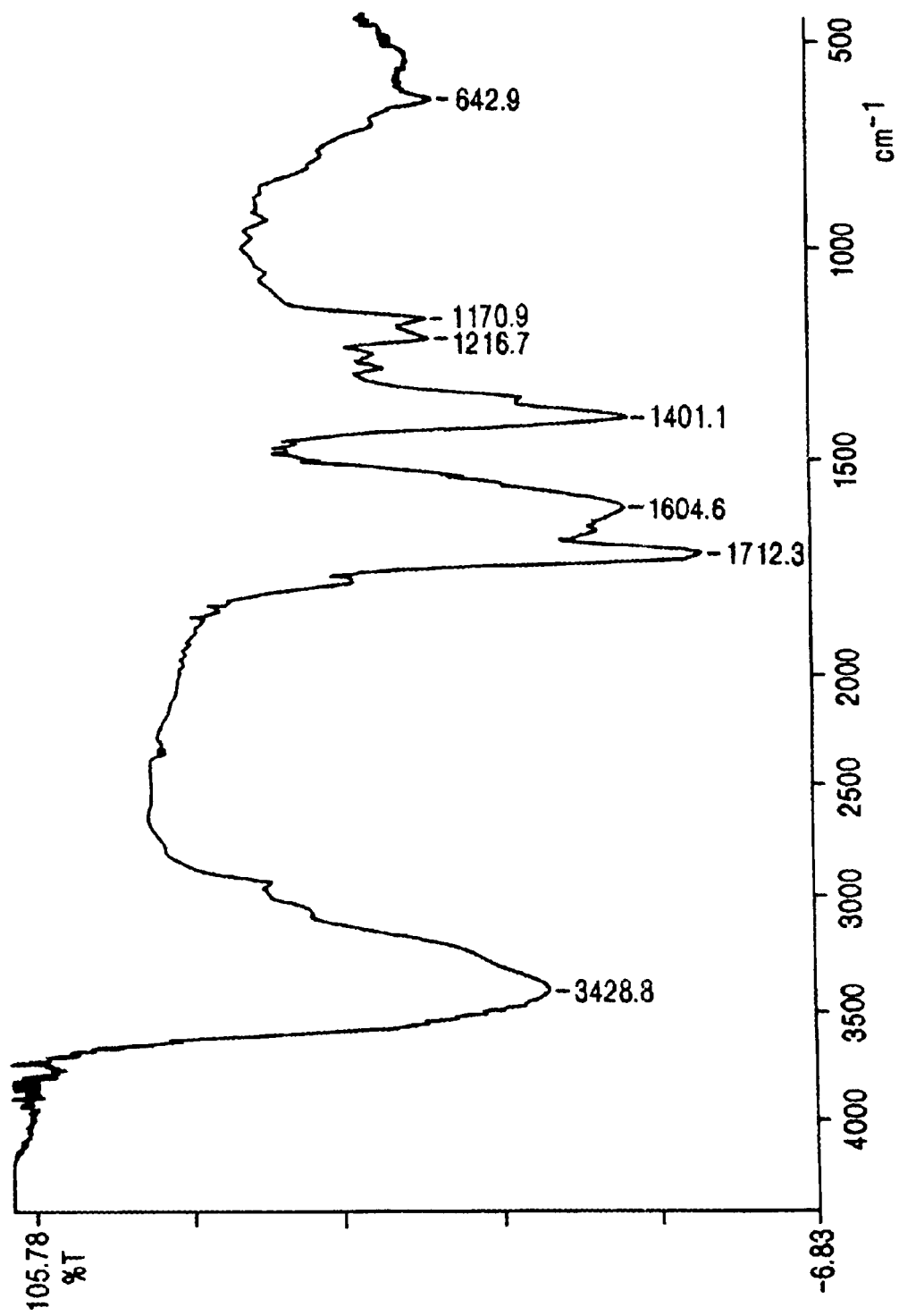
FIG. 8. Infrared spectrum of the 1:1 copolymer of monosodium aspartate and succinimide, produced via thermal polymerization at 220° C. for 2 hours of the monomer preparation of FIG. 6, the 1:1 molar ratio of monosodium aspartate and aspartic acid (prepared from a solution of monoammonium aspartate). Note the imide signal at ~1716 cm$^{-1}$ and the amide signals in the region of 1600 cm$^{-1}$. Also prominent is the carboxylate signal at ~1400 cm$^{-1}$. Notable by their absence are signals in the fingerprint region (<1000 cm$^{-1}$), indicating the absence of unreacted monomers.

The product polymer was beige in color. The yield was 11.3 g. The GPC molecular weight (number average) was 1200. The material was readily soluble in water. It was also soluble to a lesser extent in 50% isopropanol in water. The infrared spectrum (FIG. 8) revealed a mixed amide/imide structure (aspartate/succinimide) in a 1:1 residue ratio.

The yield of product copolymer of aspartate and succinimide at 11.3 g was 73% of the total amount of reactant monomers (15.3 g). This was equivalent to 97% of theoretical yield, which was calculated on the basis of loss of weight upon conversion of aspartic acid (133 g/mol) to succinimide residues (97 g/mol-residue) and the loss of weight upon conversion of monosodium aspartate monohydrate (173 g/mol) to sodium aspartate residues (137 g/mol-residue). That is, 100% theoretical yield of conversion of aspartic acid to polysuccinimide is 0.729 of the amount of monomer reactant: 100% conversion of monosodium aspartate monohydrate to poly(monosodium aspartate) is 0.792 of the amount of the monomer reactant. Accordingly, 100% theoretical yield of conversion of a 1:1 monomer composition of aspartic acid and monosodium aspartate monohydrate to copoly(aspartate, succinimide) 1:1 is 0.761 of the amount of the monomer mixture.

In the following examples 11–28, the yields of products in every case fell within the range of 0.70 to 0.80 of the combined amounts of the monomer reactants. This suggested that the reactions occurred efficiently, with yields at or near theoretical.

Example 11

Thermal polymerization of the 1:1 equivalent comonomeric composition prepared from the solution of monosodium aspartate and monoammonium aspartate to produce a copolymer of sodium aspartate and succinimide by thermal treatment at 180° C.

The comonomeric composition of example 10 was thermally polymerized at 180° C. for 4 hours in a vacuum oven at a pressure of 50 mm of Hg. The reaction proceeded during this treatment as described above in example 10, although somewhat slower, producing a light sandstone-colored material.

The yield of product copolymer of aspartate and succinimide at 11.34 g was 73.8% of the total amount of reactant monomers (15.37 g). This was equivalent to 97% of theoretical yield, which as explained above, for the 1:1 copolymer, is 0.761 of the amount of the monomer mixture.

Example 12

Thermal polymerization of the comonomeric composition prepared from the solution of monosodium aspartate and monoammonium aspartate in a 2:1 monomer ratio at 200° C.

The procedures of example 10 were followed, with adjustments as follows. In preparing the comonomeric composition, the amount of aspartic acid was 3.991 g (0.03 mole). The amount of monosodium aspartate monohydrate was 10.38 g (0.06 mole).

Figure 9:
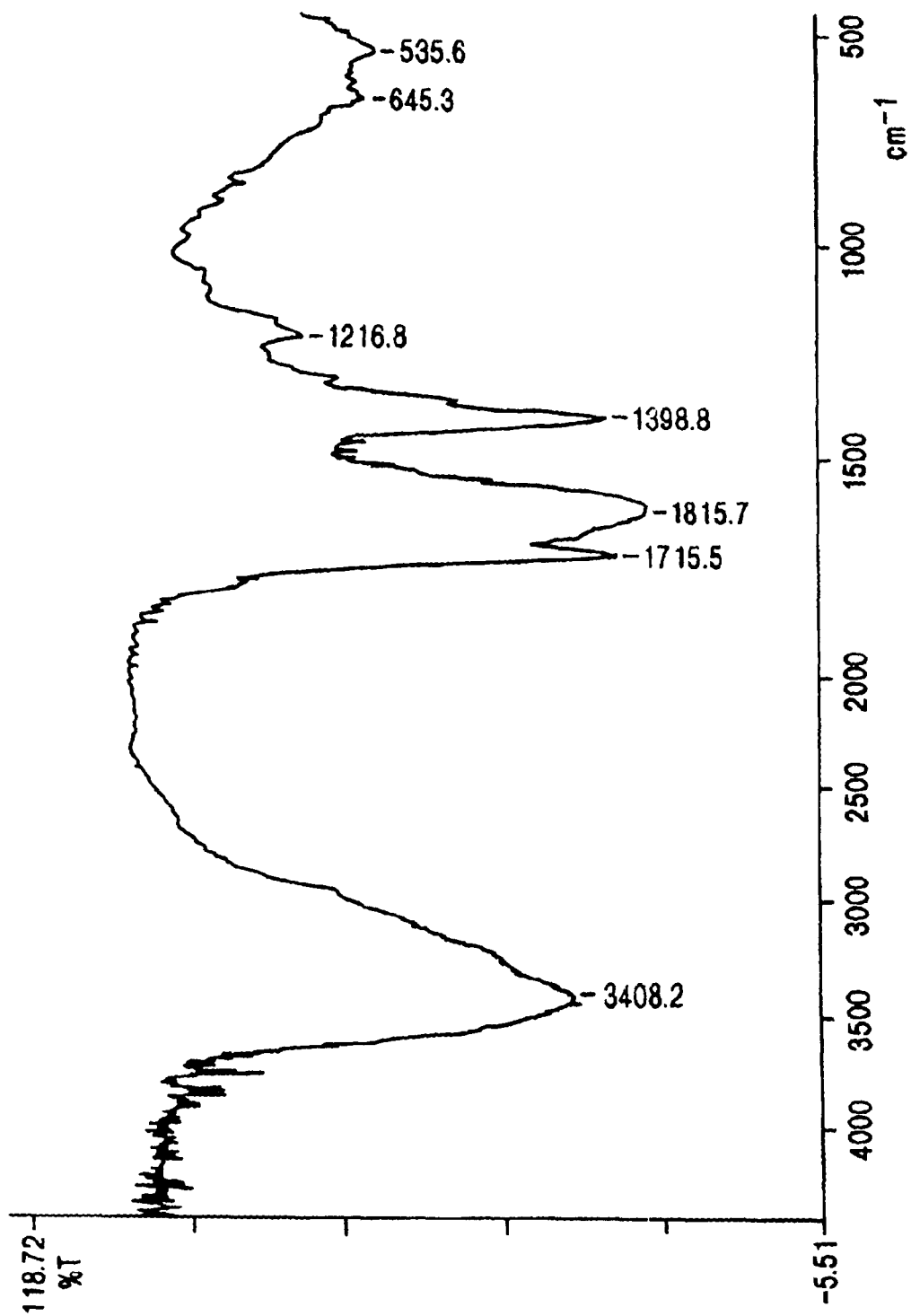
FIG. 9. Infrared spectrum of the 2:1 copolymer of monosodium aspartate and succinimide, produced via thermal polymerization of monosodium aspartate and monoammonium aspartate at 200° C. for 3 hours. The amide peaks in the region of 1600 cm$^{-1}$ became more prominent with increasing relative amounts of monosodium aspartate monomer. The imide peak at ~1716 cm$^{-1}$ tended to become accentuated with longer reaction times, as aspartic acid residues were driven more toward the succinimide form. Again, the carboxylate peak at ~1400 cm$^{-1}$ is prominent and the monomeric peaks in the fingerprint region (<1000 cm$^{-1}$) are absent.

The comonomeric salts were polymerized at 200° C. The reaction was allowed to proceed to completion for 3 hours. The GPC Mw of the product was 1000. The IR spectrum (FIG. 9) revealed the presence of residues of aspartate and succinimide in a 2:1 monomer ratio. The product was light yellow-orange in color and very soluble in water.

Example 13

Thermal polymerization of the comonomeric composition prepared from the solution of monosodium aspartate and monoammonium aspartate in a 1:2 monomer ratio at 200° C.

Figure 10:
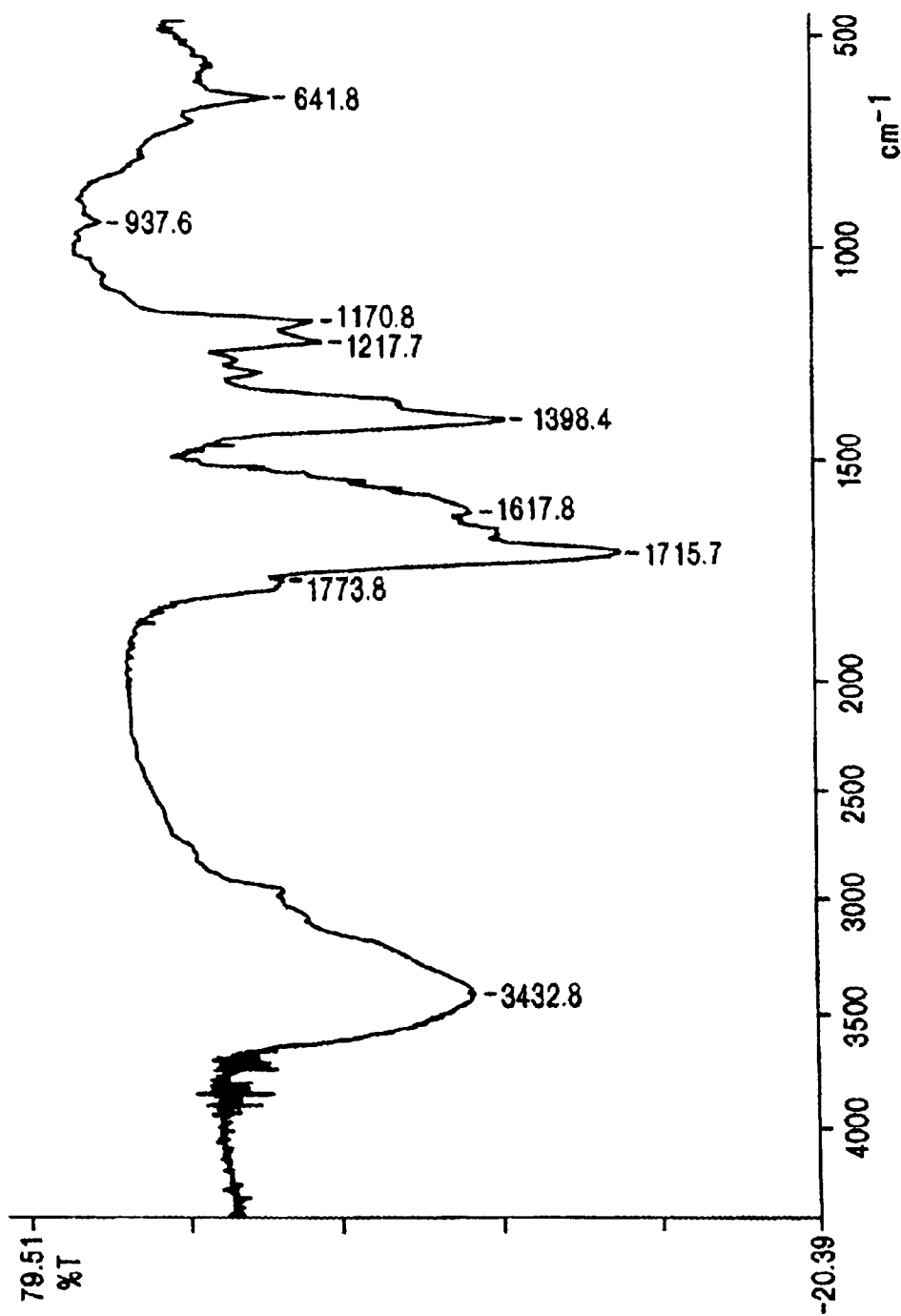
FIG. 10. Infrared spectrum of the 1:2 copolymer of monosodium aspartate and succinimide, produced via thermal polymerization of monosodium aspartate and monoammonium aspartate at 200° C. for 3 hours. In this sample, the imide peak at ~1716 cm$^{-1}$ became dominant (also favored by longer reaction times) because of the increased relative amount of monoammonium aspartate monomer, which converts to aspartic acid upon drying, which converts to succinimide upon thermal polycondensation. Although the proportion of residues as aspartate, evidenced by the amide peaks in the region of 1600 cm$^{-1}$, was relatively reduced, and the insoluble imide residues were predominant, the 1:2 copolymer was water-soluble nonetheless. Also prominent were the carboxylate peak at ~1400 cm$^{-1}$, and an anhydride doublet at 1213 and 1170 cm$^{-1}$, which becomes increasingly evident with increasing levels of succinimide (a type of anhydride) residues.

The procedures of example 12 were followed, except reversing the molar amounts of the reactant monomers. That is, the amount of monosodium aspartate monohydrate was 5.19 g (0.03 mole) and the amount of aspartic acid was 7.98 g (0.06 mole). The GPC Mw of the product was 1000. The IR spectrum (FIG. 10) revealed the presence of residues of aspartate and succinimide in a 1:2 monomer ratio. The product was soluble in water.

Example 14

Thermal polymerization of the comonomeric composition prepared from the solution of monosodium aspartate and monoammonium aspartate in a 3:1 monomer ratio at 200° C. for 4 h without vacuum.

Figure 11:
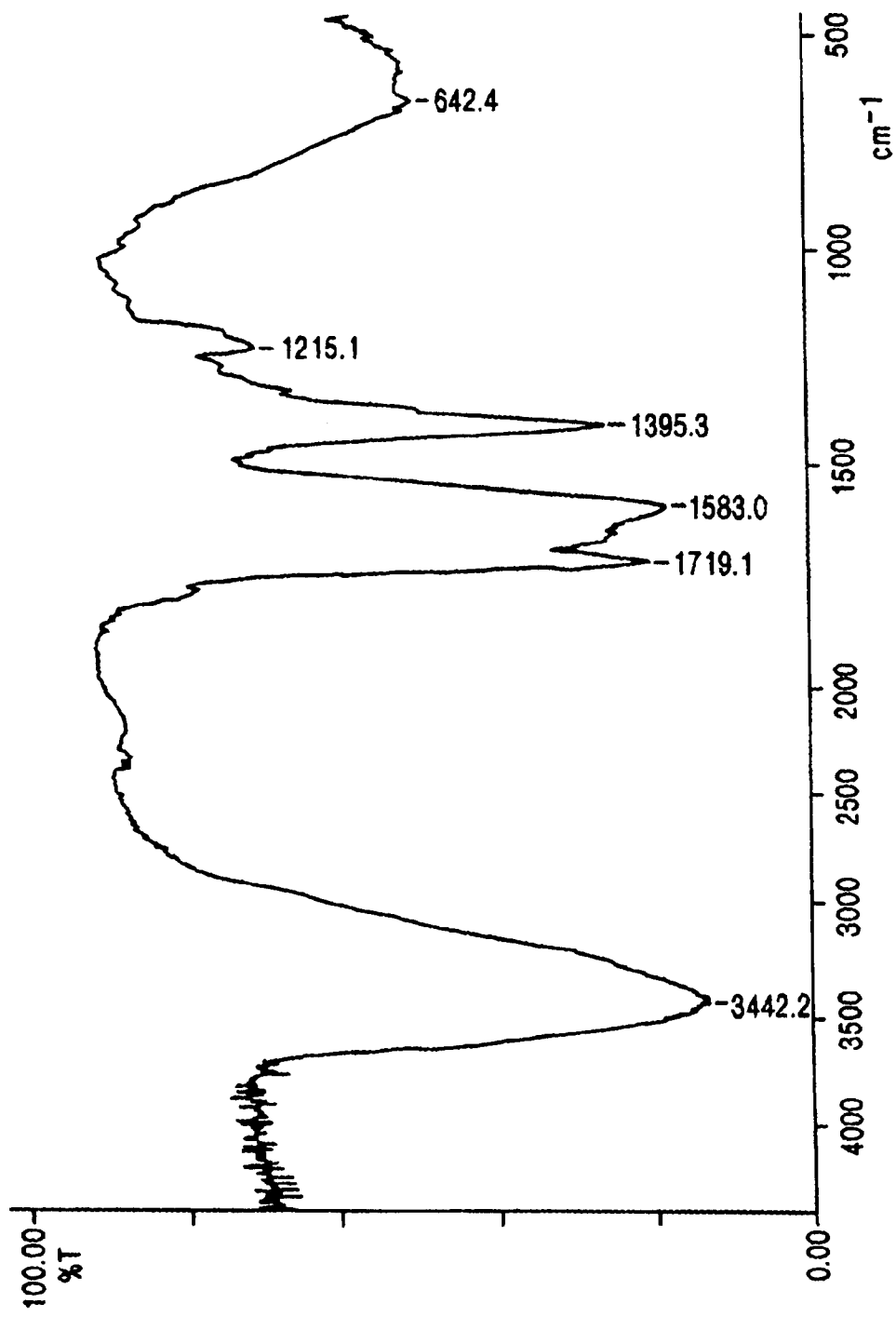
FIG. 11. Infrared spectrum of the 3:1 copolymer of monosodium aspartate and succinimide.

The procedures of example 12 were followed, except that the molar amounts of the reactant monomers were changed. That is, the amount of monosodium aspartate monohydrate was 10.38 g (0.06 mole) and the amount of aspartic acid was 2.66 g (0.02 mole). The GPC Mw was 1500. The IR spectrum (FIG. 11) revealed the presence of residues of aspartate and succinimide in a 3:1 monomer ratio. The product was very soluble in water, but was somewhat darker in color, although still a light tan, as compared to products prepared in partial vacuums.

Example 15

Thermal polymerization of the comonomeric composition prepared from the solution of monosodium aspartate and monoammonium aspartate in a 1:3 monomer ratio at 200° C. for 4 h without vacuum.

Figure 12:
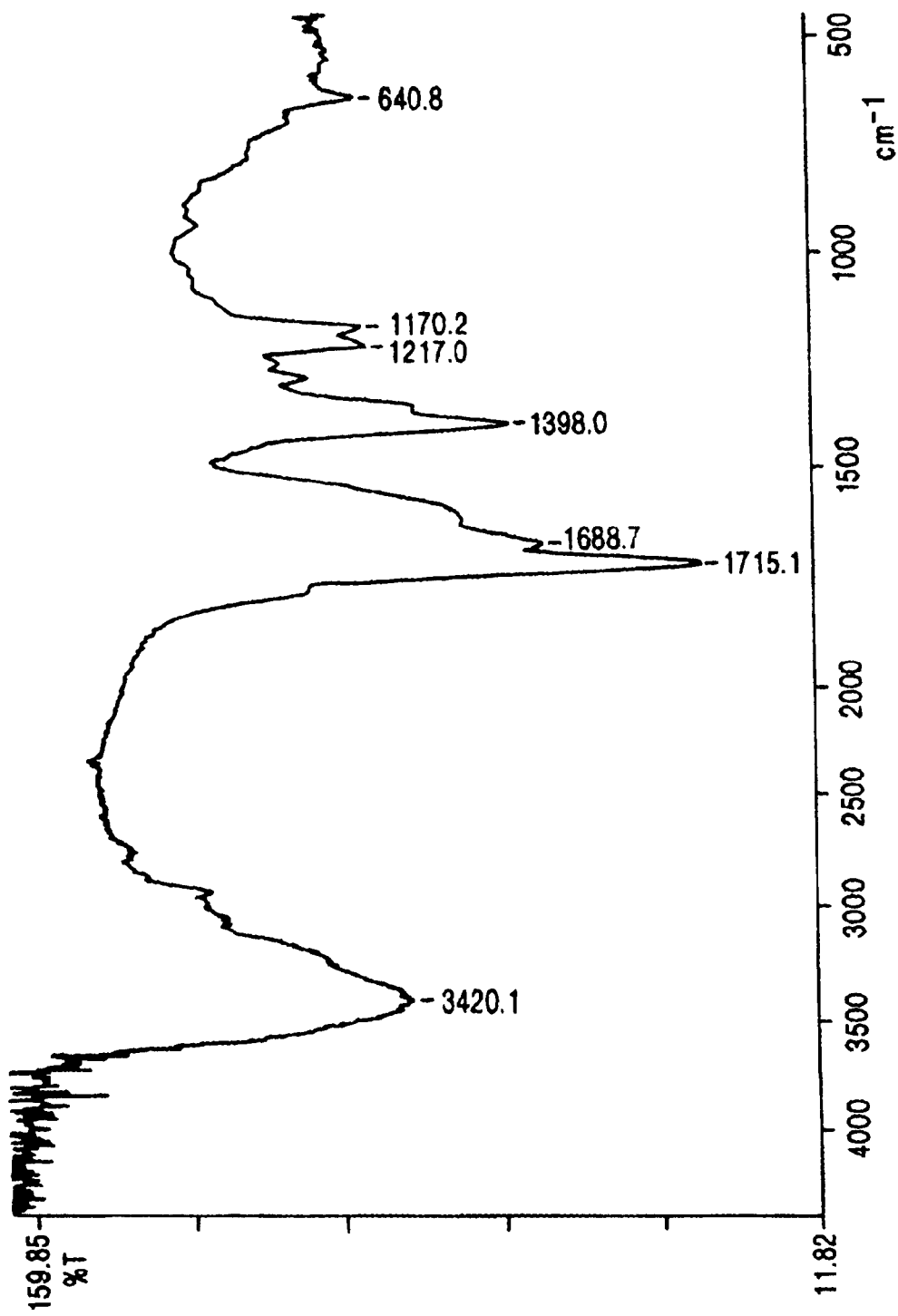
FIG. 12. Infrared spectrum of the 1:3 copolymer of monosodium aspartate and succinimide.

The procedures of example 14 were followed, except that the molar ratio of the reactant monomers was reversed. That is, the amount of monosodium aspartate monohydrate was 4.325 g (0.025 mole) and the amount of aspartic acid was 9.975 g (0.075 mole). The GPC Mw was 1800. The IR spectrum (FIG. 12) revealed the presence of residues of aspartate and succinimide in a 1:3 monomer ratio. The product was soluble in water, again with a somewhat darker tan color than products prepared in partial vacuums.

Example 16

Thermal polymerization of the comonomeric composition prepared from a solution of monosodium aspartate and monoammonium aspartate in a 4:1 monomer ratio at 200° C. for 4 h.

The procedures of example 14 were followed, except that the molar ratio of the reactant monomers was changed. That is, the amount of monosodium aspartate monohydrate was 3.46 g (0.02 mole) and the amount of aspartic acid was 0.665 g (0.005 mole), prepared as a slurry in 10 ml of water in a 50 ml beaker, then treated with 3.2 ml of the $NH_4OH$ solution (1.59 M, a 1:10 dilution of the 30% stock solution). The GPC Mw-was 1200. The IR spectrum (not shown) revealed the presence of residues of aspartate and succinimide in a 4:1 monomer ratio. The product was soluble in water, with an orange-brownish color.

Example 17

Thermal polymerization of the comonomeric composition prepared from a solution of monosodium aspartate and monoammonium aspartate in a 1:4 monomer ratio at 200° C. for 4 h.

The procedures of example 16 were followed except that the ratio of monomer reactants was reversed. That is, the amount of monosodium aspartate monohydrate was 1.038 g (0.006 mole) and the amount of aspartic acid was 3.192 g (0.024 mole). The GPC Mw was 1200. The IR spectrum (not shown) revealed the presence of residues of aspartate and succinimide in a 1:4 monomer ratio. The product retained significant solubility in water, even with an elevated succinimide content, and was an orange-brownish color.

Example 18

Thermal polymerization of an intimate admixture of aspartic acid and sodium bicarbonate in a 1:1 equivalent ratio at 220° C.

The water of condensation creates a vapor phase during the polymerization of aspartic acid. In the presence of sodium bicarbonate, bicarbonate anion can enter a transitory aqueous state, with sodium cation also solubilized momentarily. The bicarbonate decomposes in the presence of heat and water vapor to release $CO_2$ and water, further stirring the admixture through gaseous emission. The sodium can become a counterion to some of the aspartic residues in the form of monosodium aspartate, thus generating an intimate mixture of aspartic acid and monosodium aspartate. Upon thermal polymerization, this intimate mixture converts to the copolymer of aspartate and succinimide.

An amount of 6.65 g of aspartic acid (0.05 mole, MW 133, Sigma Chemical, L isomer) was pulverized with 4.2 g of $NaHCO_3$ by mortar and pestle, then placed in a 600 ml beaker. The intimate admixture was polymerized at 220° C. for 3 hours in a vacuum oven at a pressure of 50 mm of Hg.

Figure 13:
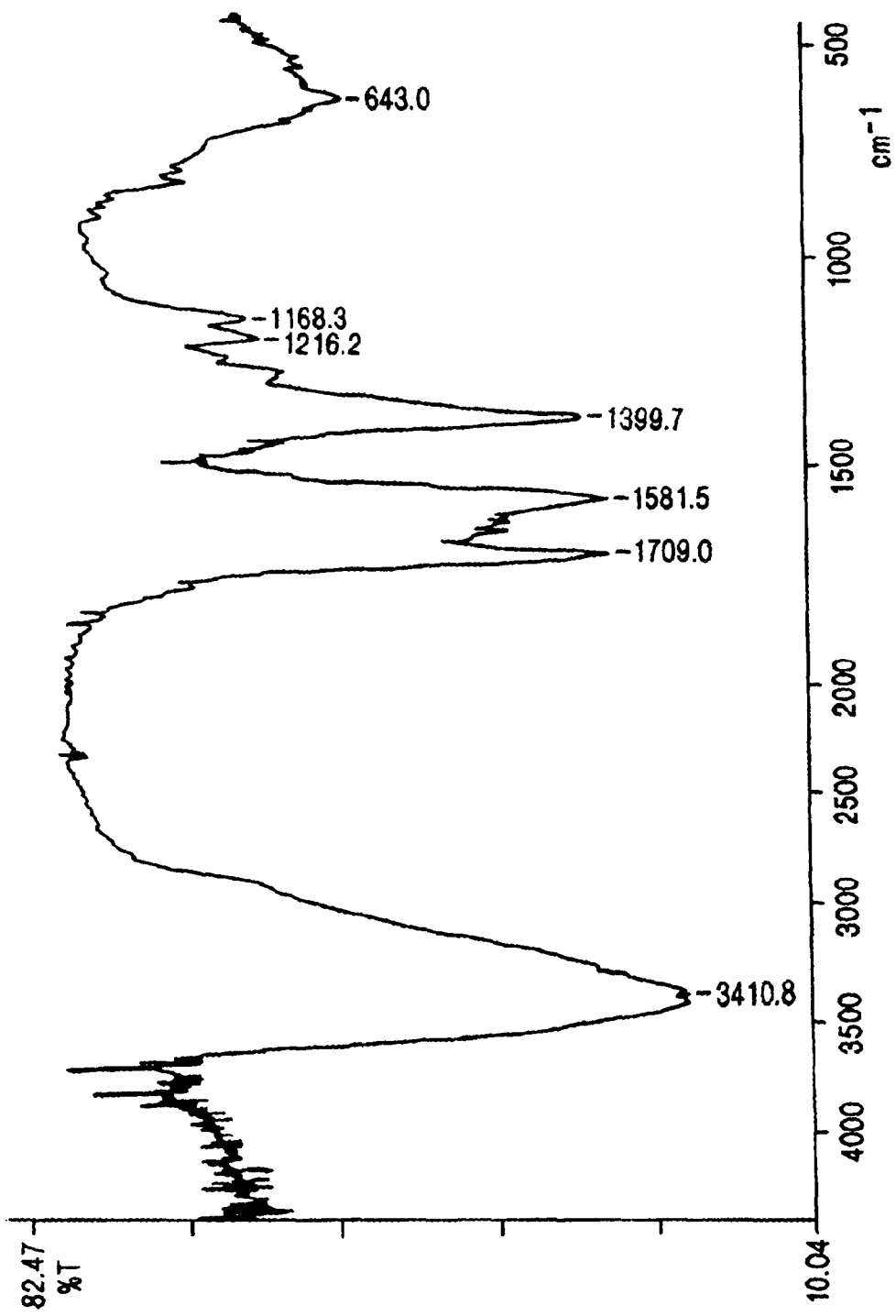
FIG. 13. Infrared spectrum of a copolymer of monosodium aspartate and succinimide prepared from a 1:1 comonomeric preparation of an intimate composition of aspartic acid and sodium bicarbonate.

The IR spectrum (FIG. 13) of the product revealed the presence of both aspartate and succinimide residues.

Example 19

Thermal polymerization of the comonomeric composition prepared from a solution of maleic acid, ammonia, and a nonalkaline salt of sodium sulfate at 200° C.

In a 250 ml reagent bottle, an amount of 69 ml (0.11 mole) of a 10% solution of concentrated ammonium hydroxide (15.9 M) was slowly added with smooth stirring to 9.8 (0.1 mole) of maleic anhydride in 18 ml (1 mole) of water at 60° C. The bottle was capped and the solution allowed to react for 2 hours. Next, 0.025 mole (3.55 of $Na_2SO_4$ (Mw 142) was added as 14.2 ml of a 25% by weight aqueous solution. The solution was poured into a 1 liter beaker and dried overnight at 120° C. to form a hardened puck, then polymerized at 200° C. for 2 hours.

The IR spectrum of the product polymer revealed the presence of both aspartate and succinimide residues.

Example 20

Thermal polymerization of the comonomeric composition prepared from a solution of maleic acid and ammonia, plus NaOH, at 200° C.

Figure 14:
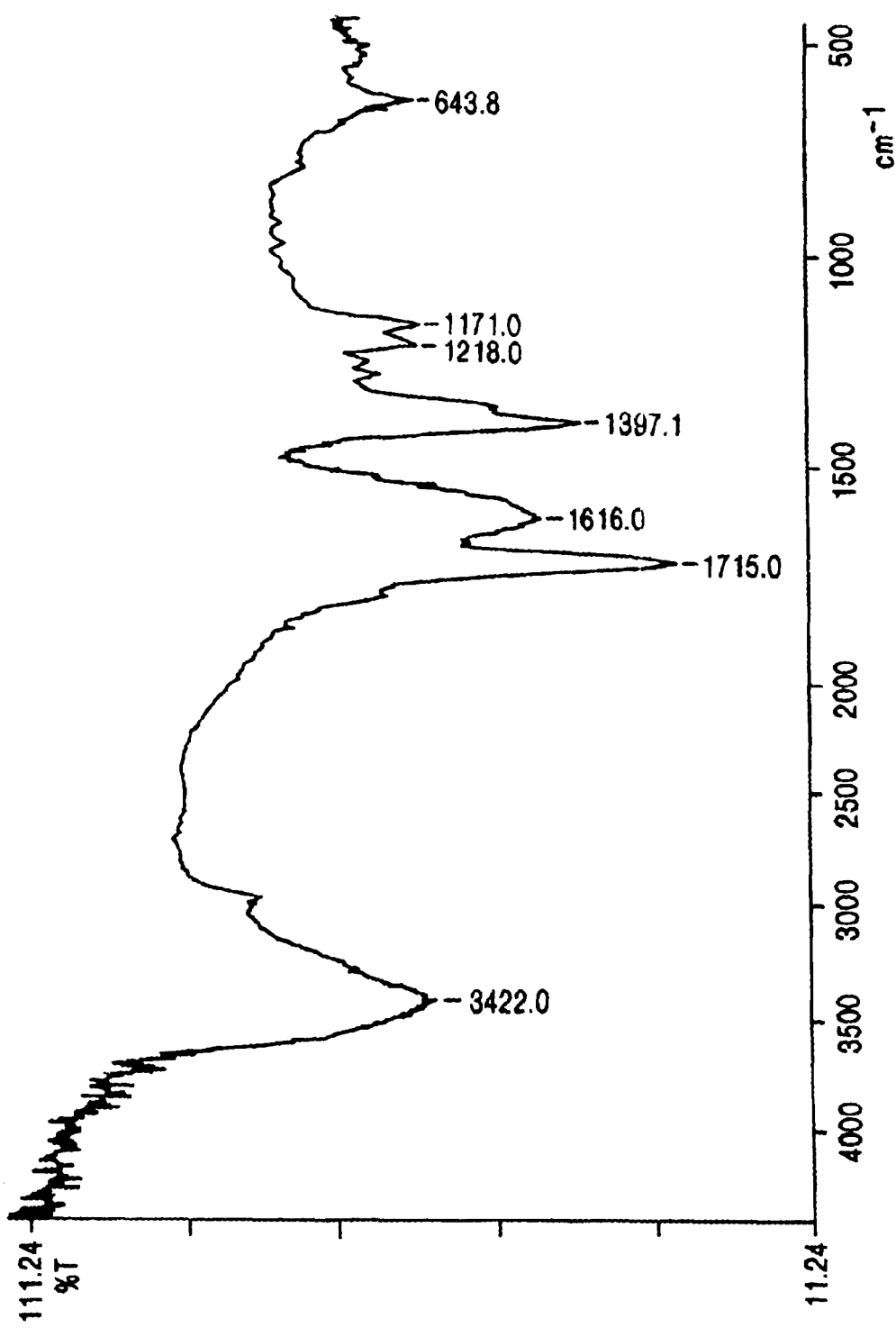
FIG. 14. Infrared spectrum of a copolymer of monosodium aspartate and succinimide prepared from a solution of maleic acid and ammonia in a 1:1.1 equivalent ratio plus heat, followed by addition of 0.5 equivalent of sodium hydroxide, followed by drying to form the salt of the comonomeric preparation.

The procedures of example 19 were followed except that the solution of maleic, ammonia, and water was treated with 0.05 mole of NaOH added as 5 ml of 10 N NaOH, rather than by addition of sodium sulfate. The IR spectrum (FIG. 14) of the product polymer revealed the presence of both aspartate and succinimide residues.

Example 21

Thermal polymerization of the comonomeric composition prepared from a solution of monoammonium aspartate and lysine in a 1:1 monomer ratio at 180° C.

Figure 15:
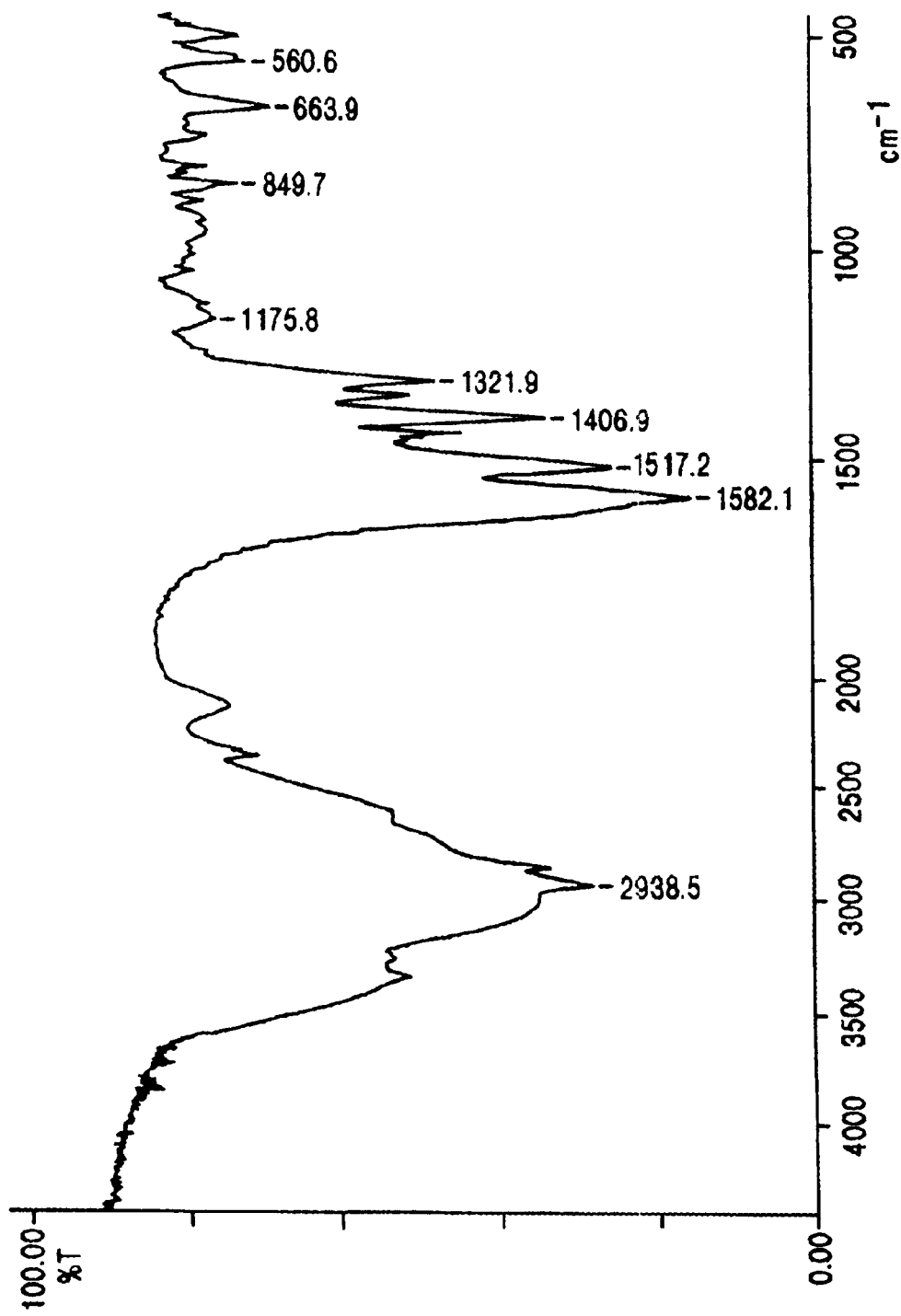
FIG. 15. Infrared spectrum of L-lysine (free base, zwitterion).

An amount of 6.65 g of aspartic acid (0.05 mole, MW 133, Sigma Chemical, L isomer) was slurried with magnetic stirring in 50 ml $H_2O$ in a 1 liter beaker. An equivalent amount of $NH_4OH$ (32 ml of a 1:10 dilution of concentrated ammonium hydroxide, 30% solution, 15.9 M) was added, dissolving the aspartic acid and converting it to monoammonium aspartate in solution. To this was added 7.31 g (0.05 mole) of lysine (free base, Mw 146.2, Sigma Chemical, L-isomer: see the IR spectrum of FIG. 15), which readily dissolved. The solution was oven-dried at 120° C. overnight to form a solid, light amber, glassy puck.

The material was polymerized at 180° C. for 3 hours in a vacuum oven at 50 mm of Hg. The water of condensation was vented occasionally by releasing the vacuum, which resulted in a collapse of the rising mass of the condensate.

The product polymer was insoluble in water, presumably due to crosslinking via lysine residues. The IR spectrum revealed the presence of imide residues.

Example 22

Thermal polymerization of a comonomeric composition prepared from a solution of aspartic acid and lysine in a 1:1 monomer ratio at 180° C.

The procedures of example 21 were followed except that the aspartic acid slurry was not neutralized with ammonium hydroxide. Rather the lysine itself served to neutralize and solubilize the aspartic acid.

The product polymer was insoluble in water. The IR spectrum revealed the presence of imide residues.

Example 23

Thermal polymerization of a comonomeric composition prepared from a solution of monosodium glutamate and monoammonium aspartate in a 1:1 monomer ratio at 220° C.

Glutamic acid often is regarded as an inefficiently polymerizable monomer because it forms a melt of a cyclic pyroglutamic condensate of itself upon heating, thus removing its amine group and one carboxylic group from further chain lengthening, condensation bonds. However, addition of sodium to block the cyclizing reaction can promote incorporation of monosodium glutamate into polyamino acids. By forming an intimate, dry composition of aspartic acid (dried from ammonium aspartate in solution) and monosodium glutamate, it is possible to condense these monomers into a polymer of succinimide and monosodium glutamate.

An amount of 6.65 g of aspartic acid (0.05 mole. MW 133. Sigma Chemical, L isomer) was slurried with magnetic stirring in 50 ml $H_2O$ in a 1 liter beaker. An equivalent amount of $NH_4OH$ (32 ml of a 1:10 dilution of concentrated ammonium hydroxide. 30% solution, 15.9 M) was added, dissolving the aspartic acid and converting it to monoammonium aspartate in solution. To this was added 9.35 g (0.05 mole) of monosodium glutamate (monohydrate, Mw 187, Sigma Chemical, L-isomer), which readily dissolved. The solution was oven-dried at 120° C. overnight to form a solid, clear, glassy puck.

The material was next thermally polymerized at 220° C. for 2 hours in a vacuum oven at a pressure of 50 mm of Hg. During this treatment, the glassy puck of the intimate composition of sodium salts of aspartate and glutamate, along with their acid forms, initially boiled for a few moments, driving off residual water of solution, then as the temperature of the material equilibrated with the ambient temperature of the oven, the polymerization began. This rising mass of the condensate was collapsed from time to time by venting, the vacuum.

A water-soluble polymer was produced. The IR spectrum (not shown) revealed tile presence of imide residues.

Example 24

Thermal polymerization of a comonomeric composition prepared from a solution of aspartic acid, monosodium glutamate, and lysine in a 1:1:1 monomer ratio at 220° C.

Terpolymers and polymers with more complex mixtures of monomers can also be produced that contain imide residues.

An amount of 6.65 g of aspartic acid (0.05 mole, MW 133. Sigma Chemical, L isomer) was slurried with magnetic stirring in 50 ml $H_2O$ in a 1 liter beaker. To this was added 7.31 g (0.05 mole) of lysine (free base, Mw 146.2. Sigma Chemical, L-isomer), which was readily dissolved and also neutralized and solubilized the aspartic acid. Next, 9.35 g (0.05 mole) of monosodium glutamate (monohydrate, Mw 187, Sigma Chemical, L-isomer) was added, which also readily dissolved. The solution was oven-dried at 120° C. overnight to form a solid, light amber, glassy puck.

The material was next thermally polymerized at 220° C. for 2 hours in a vacuum oven at a pressure of 50 mm of Hg. The rising mass of the condensate was collapsed from time to time during the first hour by venting the vacuum.

The IR spectrum (not shown) of the product polymer revealed the presence of imide residues. The imide-containing polyamino acid was insoluble in water.

Example 25

Thermal polymerization of a comonomeric composition prepared from a solution of monosodium aspartate, ammonium aspartate, and lysine in a 1:1:1 monomer ratio at 200° C. for 4 h in a partial vacuum.

Figure 16:
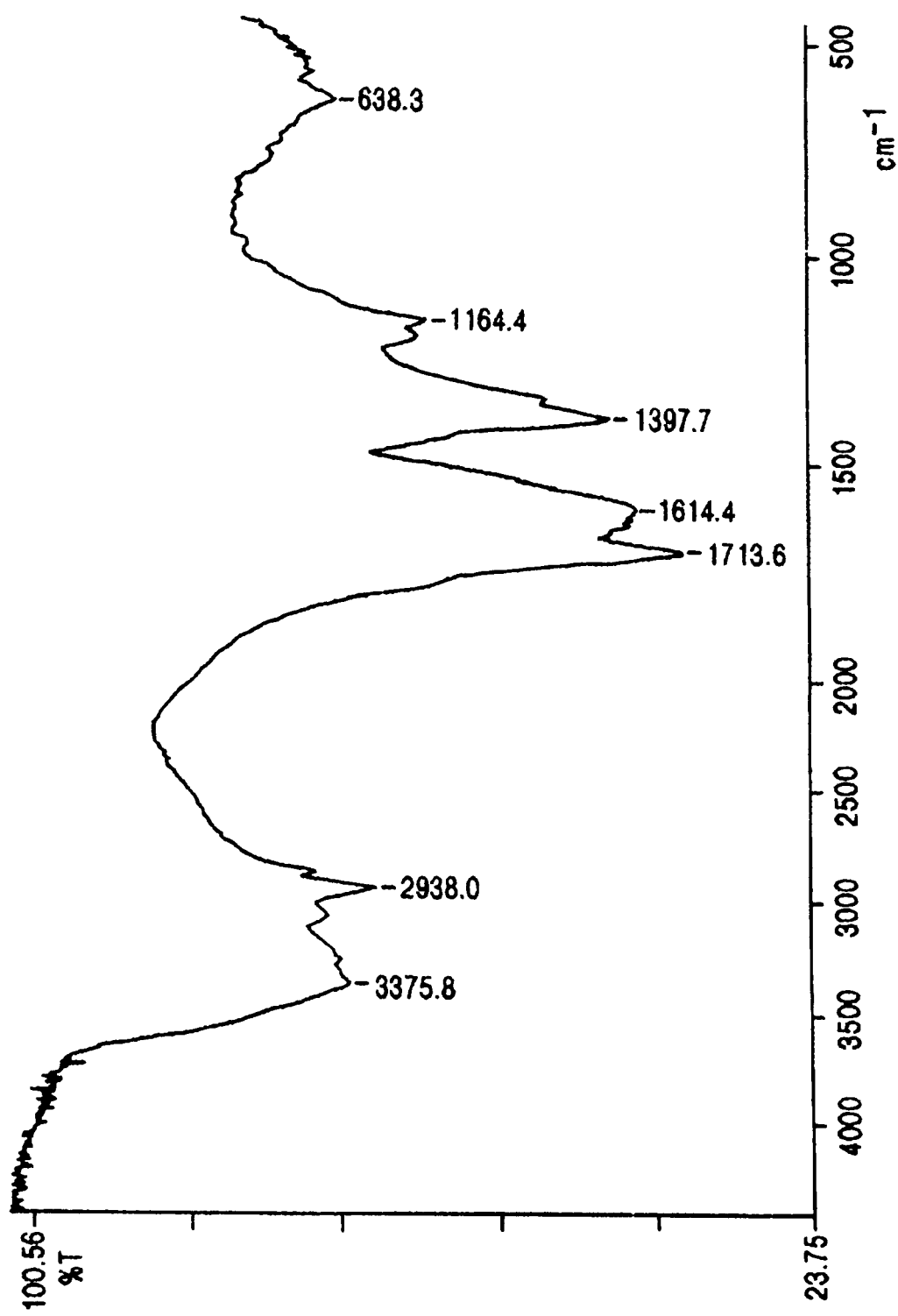
FIG. 16. Infrared spectrum of the 1:1:1 copolymer of monosodium aspartate, succinimide, and lysine.

The comonomeric composition of example 5 was polymerized in a vacuum oven at a pressure of 50 mm Hg for 4 h at 200° C. The IR spectrum (FIG. 16) of the product material revealed the presence of imide residues. The material was insoluble in water, even at 1 mg/ml, but was somewhat gelled. Upon mild alkaline ring-opening of the imide residues at pH 10, 60° C. for 1 to 2 h, the material remained insoluble at 1 mg/ml, but increased in the amount of its gelling properties.

The polymeric material presumably is crosslinked via the lysine residues, forming a continuous network that interacts readily with water but is too large to be solubilized. Thus the Mw of the polymeric material is very high, although not assignable exactly, with each particle possibly equivalent to a continuous, covalently linked "molecule".

Example 26

Thermal polymerization of a comonomeric composition prepared from a solution of monosodium aspartate, ammonium aspartate, and lysine in a 1:1:0.6 monomer ratio at 200° C. for 4 h in a partial vacuum.

The comonomeric composition of example 6 was polymerized according to the procedures of example 25. As described in example 25, the product material was an imide-containing polyamino acid that had gelling properties, but was largely water-insoluble. Upon the ring-opening treatment, the material increased in its gelling properties, rendering the solution at 1 mg/ml partially gelled and noticeably viscous.

Example 27

Thermal polymerization of a comonomeric composition prepared from a solution of monosodium aspartate, ammonium aspartate, and lysine in a 1:1:0.5 monomer ratio at 200° C. for 4 h in a partial vacuum.

Figure 17:
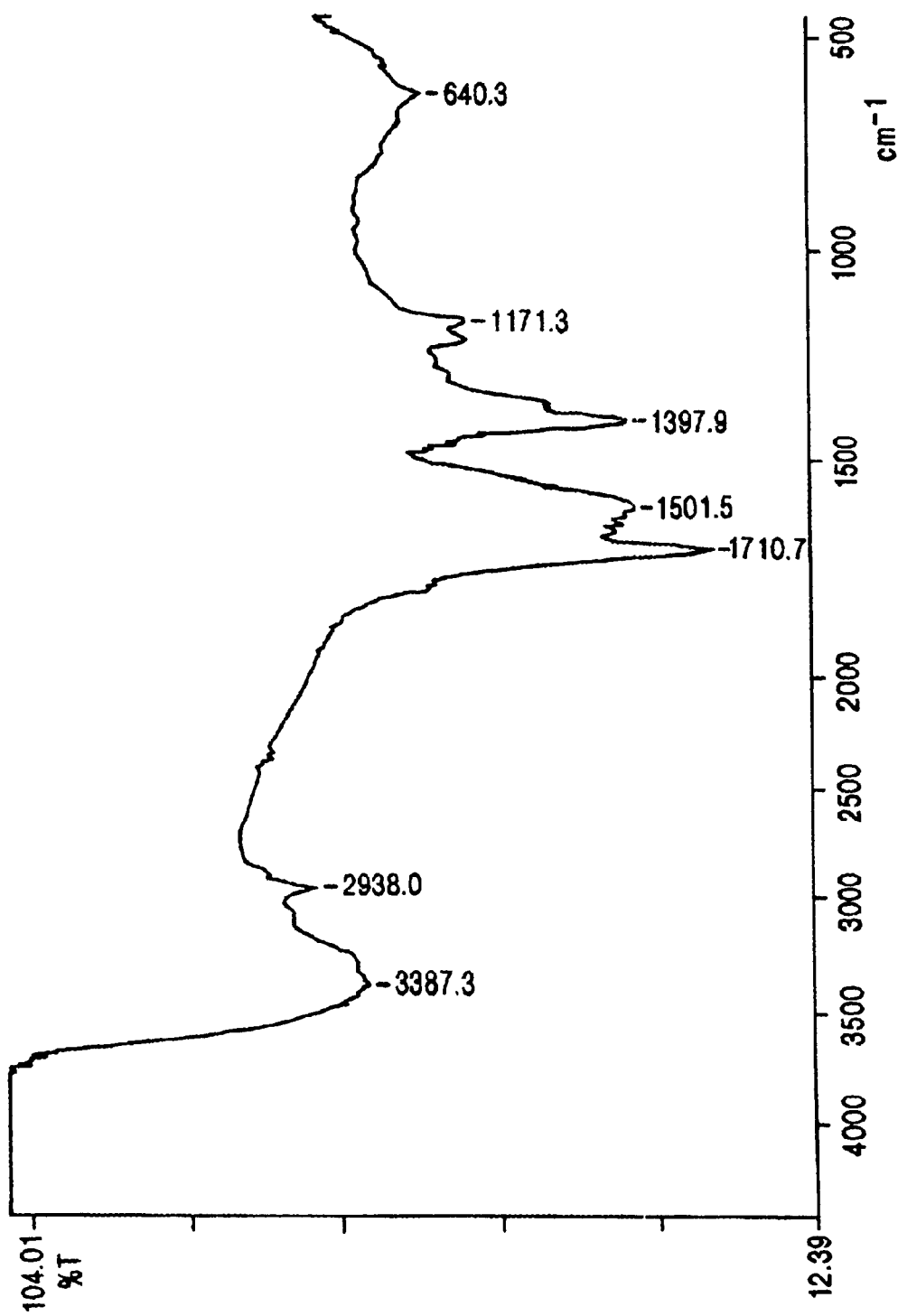
FIG. 17. Infrared spectrum of the 1:1:0.5 copolymer of monosodium aspartate, succinimide, and lysine.

The comonomeric composition of example 7 (oven-dried at 120° C.) was polymerized according to the procedures of example 25. Again, the IR spectrum (FIG. 17) of the polymer product revealed the presence of imide residues. In this case, the material was mostly soluble in water at 1 mg/ml. The GPC Mw of the soluble fraction of the imide-containing polyamino acid was 1500. A lesser fraction of the material formed a viscous, loose, aqueous gel.

Example 28

Thermal polymerization of a lyophilized comonomeric composition prepared from a solution of monosodium aspartate, ammonium aspartate, and lysine in a 1:1:0.5 monomer ratio at 200° C. for 4 h in a partial vacuum.

The comonomeric composition of example 8 was polymerized according to the procedures of example 27, except that the dry, intimate composition of monosodium aspartic, aspartic acid (dried from ammonium aspartate in solution), and lysine was prepared by lyophilization rather than oven-drying at 120° C. The product material was very similar to the material of example 27, indicating that the drying step via boiling during preparation of the comonomeric composition did not adversely affect the comonomeric preparation.

The preceding examples can be repeated with similar success by substituting the generically or specifically described reactants and or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

References

Adler, David E., M. B. Freeman, J. M. Lipovsky, and Y. H. Paik. 1995. Acid catalyzed process for preparing amino acid polymers. U.S. Pat. No. 5,457,176: 1–26.

Adler, David E., M. B. Freeman, J. M. Lipovsky, and Y. H. Paik. 1996. Acid catalyzed process for preparing amino acid polymers. U.S. Pat. No. 5,552,514.

Allen. A. J. 1999. Highly branched polyamidoamines and their preparation. U.S. Pat. No. 5,902,862.

Alpert, Andrew J. 1985. Chromatographic support material. U.S. Pat. No. 4,517,241.

Baur, Richard, W. Bertleff, H. Jaeger, A. Funhoff, M. Kroner, and G. Schornick. 1999. Use of modified polyaspartic acids in washing agents. U.S. Pat. No. 6,001,798.

Bayer, Roland, Wolfgang Koch, and Klaus Szablikowski. 1999. Process for the preparation of retention and dewatering, agents based on polyamino-ethers. U.S. Pat. No. 5,886,095.

Boehmke, Gunther. 1989. Polyaspartic acid from maleic acid and ammonia. U.S. Pat. No. 4,839,461.

Chang, Ching-Jen, and Graham Swift. 1999. Crosslinked poly(amino acids) and method of preparation. U.S. Pat. No. 5,955,549.

Chou, Yueting, Dennis J. Kalota, and David Albert Martin. 1999. Crosslinked polyaspartate salts a process for their production. U.S. Pat. No. 5,981,761.

Chou, Yueting, Timothy Paul Feast, and Jingen Zhang. 2000. Superabsorbing compositions and processes for preparing same. U.S. Pat. No. 6,027,804.

Chou, Yueting, Timothy Paul Feast, Jingen Zhang, and David Sikora. 1999. Superabsorbing fibers and films and processes for preparing same. U.S. Pat. No. 5,997,791.

Dorian, Randel E. and K. C. Cochrum. 1997. Non-fibrogenic high mannuronate alginate coated transplants, processes for their manufacture, and methods for their use. U.S. Pat. No. 5,693,514: 1–12.

Duncum, Simon N., A. R. Edwards, K. James, and C. G. Osborne. 1996. Hydrate inhibitors. World Patent WO 96/29502.

Du Vosel, Annick, F. Francalanci, and P. Maggioriotti. 1997. Polyaminoacids as builders for formulations of detergents. U.S. Pat. No. 5,658,872.

Engel, Jurgen, Wolfgang Deger, Thomas Reissmann, Gunter Losse, Wolfgang Naumann, and Sandra Murgas. 2000. Immobilized and activity-stabilized complexes of LHRH antagonists and processes for their preparation. U.S. Pat. No. 6,022,860.

Ferencz, A. 1998. Preparation and use of polyaspartamides. Patent DE19720771.

Freeman, M. B., Y. H. Paik, E. S. Simon, and G. Swift. 1993. Enhancing detergent performance with polysuccinimide. U.S. Pat. No. 5,266,237.

Futatsugi, M., and K. Gushi. 1998. Heat-stable and water soluble modified enzymes. U.S. Pat. No. 5,834,273.

Gelosa, D., R. Ruggieri, A. Sliepcevich, and F. Codinola. 1999. Polymers of aspartic acid with sequestering activity process for their preparation and use thereof. U.S. Pat. No. 5,936,121.

Gleich, G. J. 1996. Method for the treatment of eosinophil-associated conditions with anionic polymers. U.S. Pat. No. 5,498,410.

Groeschl, A., T. Groth, W. Joentgen, and W. Zarges. 1998. Membrane process for treatment of aqueous feeds. International Patent WO 98/22205 A1.

Grollier, J. and C. Fourcadier. 1988. Cosmetic composition for delaying the appearance of an oily aspect of hair. U.S. Pat. No. 4,735,797: 1–20.

Groth, T., W. Joentgen, G. Boehmke, G. Schmitz, and H. Traenckner. 1994. Process for the preparation of polysuccinimide and polyaspartic acid. U.S. Pat. No. 5,371,180.

Groth, Torsten, W. Joentgen, D. Jovcic, P. Wagner, and H. Traenckner. 1996. Process for the preparation of polysuccinimide. U.S. Pat. No. 5,493,004.

Groth, T., W. Joentgen, N. Müller, and U. Liesenfelder. 1997. Process for preparing polysuccinimide and polyaspartic acid. U.S. Pat. No. 5,610,255.

Groth, Torsten, W. Joentgen, B. Koenemund, F. Lesszinsky, M. Riegels, U. Vogt, and K. Walz. 1998. Biodegradable bath stabilizer and leveling agent for dyeing or printing textile. International Patent DE 19635061 A1.

Gruning, Burghard, Harald Rau, Jorg Simpelkamp, and Christian Weitemeyer. 1999. Polyamino acid ester copolymers. U.S. Pat. No. 5,910,564.

Hall, Robin Gibson, and Alan David Willey. 1999. Detergent compositions comprising stabilised polyamino acid compounds. U.S. Pat. No. 5,902,782.

Hallam, M., G. T. Shouldice, and J. J. Guth. 2000. Use of derivatives of polyamino acids as emulsifiers stabilizers in aqueous free radical emulsion polymerization. U.S. Pat. No. 6,143,817.

Hann, William Mathis, Y. H. Paik, S. T. Robertson, and G. Swift. 1997. Method of inhibiting sulfate scale in aqueous systems using poly (amino acids). U.S. Pat. No. 5,658,464: 1–16.

Harada, K. 1959. Polycondensation of thermal precursors of aspartic acid. Journal of Organic Chemistry 24, 1662–1666.

Harada, Yukiko, H. Shinoda, M. Sukegawa, and H. Tamatani. 1997. Polyaspartic acid Zwitterionic derivatives, preparation processes thereof, hair-treating compositions and cosmetic compositions. U.S. Pat. No. 5,686,066: 1–74.

Harms, David J. and A. R. Y. Meah. 1996. Method and composition for preservation of cut flowers. U.S. Pat. No. 5,580,840: 1–6.

Harrison, James J. and W. R. Ruhe, Jr. 2000. Polyalkylene polysuccinimides and post-treated derivatives thereof. U.S. Pat. No. 6,015,776.

Hewer, Lutz, Winfried Joentgen, and Torsten Groth. 1999. Timber preservative containing a copper compound. U.S. Pat. No. 5,874,025.

Hewer, Lutz, Winfried Joentgen, Torsten Groth, and Ralf-Johann Moritz. 1999. Use as antifreeze of polymers with recurring succinyl units. U.S. Pat. No. 5,942,150.

Hogan, Joseph C. Jr. 1999. Aminimide-containing molecules and materials as molecular recognition agents. U.S. Pat. No. 5,981,467.

Hozumi, Yoshiyuki, T. Inaoka, T. Gomi, T. Goto, T. Uno, and K. Rakutani. 1997. Oil absorbent polymer and use thereof. U.S. Pat. No. 5,641,847: 1–82.

Hrkach, Jeffrey S., R. S. Langer, and N. Lotan. 1997. Functionalized polyester graft copolymers. U.S. Pat. No. 5,654,381: 1–16.

Hubbell, Jeffrey A., Chandrashekhar P. Pathak, Amarpreet S. Sawhney, Neil P. Desai, Jennifer L. Hill-West, and Syed F. S. Hossainy. 1996. Gels for encapsulation of biological materials. U.S. Pat. No. 5,573,934.

Huille, Sylvain, Alain Lemercier, and Gerard Soula. 1999. Particles based on polyamino acid(s) and capable of being used as delivery vehicles for active principle(s) and method for preparing them. U.S. Pat. No. 5,904,936.

Inaoka, Toru, H. Tahara, and M. Masahiko. 1996. Gel-like fragrance composition. U.S. Pat. No. 5,556,835.

Jacquet, Bernard, C. Papantonion, G. Land, and S. Forestier. 1982. Polyaspartic acid derivatives, their preparation and their use in cosmetic composition. U.S. Pat. No. 4,363,797: 1–12.

Jansen, B. and Joachim K., and P. Nowak. 2000. Paper finishing process using polyisocyanates with anionic groups and cationic compounds. U.S. Pat. No. 6,022,449.

Jason, Mark E. and D. J. Kalota. 1996. Microencapsulation process by coacervation. U.S. Pat. No. 5,540,927: 1–8.

Kalota, Dennis J. and D. C. Silverman. 1995. Process for metal cleaning. U.S. Pat. No. 5,443,651: 1–10.

Kalota, Dennis J., L. A. Spickard, and S. H. Ramsey. 1995. Water soluble metal working fluids. U.S. Pat. No. 5,401,428.

Kalota, Dennis J., S. H. Ramsey, and L. A. Spickard. 1997. Water soluble metal working fluids. U.S. Pat. No. 5,616,544: 1–16.

Kato, N., Y. Mori, N. Mine, S. Fujii, and N. Watanabe. 1998. Method for producing L-aspartic acid.

Kim, Son Nguyen, Axel Sanner, Peter Hossel, and Matthias Kroner. 1999. Water-soluble or water-dispersible polyaspartic acid derivatives, their preparation and their use. U.S. Pat. No. 5,925,728.

Kim, Son Nguyen, Axel Sanner, Peter Hossel, and Matthias Kroner. 1999. Water-soluble or water-dispersible polyaspartic acid derivatives, their preparation and their use. U.S. Pat. No. 5,961,965.

Koskan, L. P., A. R. Y. Meah, J. L. Sanders, and R. J. Ross. 1998. Method and composition for enhanced hydroponic plant productivity with polyamino acids. U.S. Pat. No. 5,783,523.

Krepski, Larry R., P. S. Rao, T. P. Smith, K. D. Wilson, and R. J. Kuo. 1997. Water-based pigmented inks. World Patent WO 97/43351.

Kroner, Matthias, H. Hartmann, G. Schornick, R. Baur, B. Potthoff-Karl, V. Schwendemann, and A. Kud. 1996. Preparation of polymers of aspartic acid and their use. U.S. Pat. No. 5,548,036: 1–14.

Kroner, Matthias, G. Schornick, D. Boeckh, R. Baur, B. Potthoff-Kark, V. Schwendemann, C. Schade, and A. Kud. 1997. Preparation of products of the reaction of polyaspartimide and amino acids and the use thereof. U.S. Pat. No. 5,639,832: 1–10.

Kroner, Matthias, G. Schornick, U. Strotmann, V. Schwendemann, T. Meyer, and A. Ludwig. 1999. Preparation of salts of polyaspartic acid and their use in detergents and cleaners. U.S. Pat. No. 5,886,137.

Kroner, Matthias, G. Schornick, R. Baur, A. Kud, and V. Schwendemann. 1998. Use of polyaspartic acid in detergents and cleaners. U.S. Pat. No. 5,770,553.

Lehmann, Klaus, Riger Jelitte, and J. Knebel. 1992. Polymers derived from polysuccininmide used as surface coatings for medicinals and foods. U.S. Pat. No. 5,175,285: 1–14.

Martin, David A. 1998. Production of solid polyaspartate salt. World Patent WO98/34976.

Mazo, G. Y., J. Mazo, B. Vallino, and R. J. Ross. 1999. Production of D,L-aspartic acid. U.S. Pat. No. 5,872,285

Mazo, Grigory Ya., Jacob Mazo, Barney Vallino, and Robert J. Ross. 1999. Production of polysuccinimide and polyaspartate in thioether solvents. U.S. Pat. No. 5,939,522.

Milstein, Sam J. and M. L. Kantor. 1996. Proteinoid carriers and methods for preparation and use thereof. U.S. Pat. No. 5,578,323: 1–52.

Mitsubishi. 1998. Polysuccinimide type resin mouldings. Japanese Patent JP 10139880 A.

Mitsui Toatsu. 1998. Polymer composition for containers. Japanese Patent JP 10168326 A.

Nakato, T., and M. Tomida. 1998. Amine-modified polyaspartic acid or salt thereof and process for preparing the same. European Patent EP 0 826 716 A2.

Neri, Dr. Paolo, G. Antoni, F. Benvenui, and S. Franco. 1971. Verfahren und herstellung von α-β-Poly-(asparaginsaure)-hydroxy-alkylamiden und ihre therapeutische verwendung. German Patent 2032470: 1–48.

Oda, Y. 2000. Modified polyaspartic acid, method for production thereof and use thereof. European Patent EP 0 980 883 A1.

Pohmer, Klaus, R. Weber, C. Dorzbach-Lange, K. Stachulla, H. Moretto, ands M. Wienand. 1996. Imides and their salts, as well as their use. U.S. Pat. No. 5,502,251: 1–14.

Popoff, Christine, Alwyn Nartey, Robert Gabriel, and Eric Aubay. 2000. Fabric color protection compositions and methods. U.S. Pat. No. 6,040,288.

Primeaux II, Dudley J., Robert L. Zimmerman, and Kenneth M. Hillman. 2000. Method of preparing an aliphatic polyurea spray elastomer system. U.S. Pat. No. 6,013,755.

Reilly, Eugene P., S. C. Arnold, ands A. G. Scopelianos. 1995. Reinforced absorbable polymers. U.S. Pat. No. 5,397,816.

Reiners, J., M. Schnee, T. Groth, W. Joentgen, G. Schmitz, H. Traubel, and N. Muller. 1999. Use of polyaspartic acid amides as leather auxiliary products. U.S. Pat. No. 5,885,474.

Riegels, Martin, Uwe Vogt, Klaus Walz, Fritz Lesszinsky, Bernd Konemund, Torsten Groth, and Winfried Joentgen. 1999. Composition for dyeing or printing textile materials. U.S. Pat. No. 5,902,357.

Ross, R. J., K. C. Low, and L. P. Koskan. 1995. Soluble, crosslinked polyaspartates. World Patent WO 95/35337.

Ross, Robert J., K. C. Low, L. P. Koskan, and A. P. Wheeler. 1996. Superabsorbing polymeric networks. International Patent WO 96/08523.

Sakano, K., T. Hayashi, and M. Mukouyama. 1996. Process for production of L-aspartic acid. U.S. Pat. No. 5,541,090.

Sanders, J. Larry. 1997. Polyaspartic acid and its analogues in combination with insecticides. U.S. Pat. No. 5,646,133.

Sanders, J. Larry. 1997. Polyorganic acids and their analogues to enhance herbicide effectiveness. U.S. Pat. No. 5,635,447.

Sanders, J. Larry. 1999. Treatment of tree seedlings to enhance survival rate. U.S. Pat. No. 5,935,909.

Schmidt, D. L. and R. D. Mussell. 1999. Multisolvent-based film-forming compositions. U.S. Pat. No. 5,910,532.

Schopwinkel, G., K. Butje, G. Wieghaus, R. Bathke, T. Groth, and W. Joentgen. 1998. Pigment preparations having a high solids content. U.S. Pat. No. 5,804,639.

Sherwin, M. B. and J. J. Blouin. 1985. Process for preparing L-aspartic acid. U.S. Pat. No. 4,560,653.

Shokubai, Nippon. 1999. Builders for detergents—containing polyaspartic acid derivative. Japanese Patent JP11092787.

Shokubai, Nippon. 1999. Corrosion inhibitor. Japanese Patent JP11350172.

Sikes, C. Steven. 1994. Polyamino acid dispersants. U.S. Pat. No. 5,328,690: 1–24.

Sikes, C. Steven. 1998. Absorbent gelling materials of crosslinked polyaspartate. U.S. Pat. No. 5,773,564. International patent issued and validated.

Sikes, C. S. 1999. Imide-free and mixed amide/imide thermal synthesis of polyaspartate. U.S. Pat. No. 5,981,691.

Sikes, C. Steven and A. P. Wheeler. 1985. Inhibition of inorganic or biological $CaCO_3$ deposition by poly amino acid derivatives. U.S. Pat. No. 4,534,881: 1–16.

Sikes, C. Steven and A. P. Wheeler. 1989. Inhibition of tartar deposition by polyanionic/hydrophobic peptides and derivatives thereof which have a clustered block copolymer structure. U.S. Pat. No. 4,866,161: 1–18.

Sikes, C. Steven, Thomas M. Vickers Jr., and Stephen A. Farrington. 1999. Polysuccinimide and polyaspartate as additives to cementitious materials. U.S. Pat. No. 5,908,885.

Stahl, W., M. Ahlers, A. Walch, E. Bartnik, G. Kretzschmar, S. Grabley, and R. Schleyerbach. 1995. Carbohydrate-containing polymers, their preparation and use. U.S. Pat. No. 5,470,843.

Staley, James T., I. A. Aksay, G. L. Graff, N. B. Pellerin, and T. Ren. 1996. Process for suspension of ceramic or metal particles using biologically produced polymers. U.S. Pat. No. 5,503,771.

Stevens, Kent R. and W. V. Taggart. 1996. Polyamides bearing fictionalized side chains useful as water soluble hypolipidemic agents. U.S. Pat. No. 5,516,758: 1–26.

Suau, Jean-Marc, Christian Jacquemet, and Jacques Mongoin. 1998. Polyaspartic acid salts—are used as agents to aid crushing of mineral materials. European Patent EP0860477A1.

Tang, Jiansheng, Shi-Liang Fu, and Daniel H. Emmons. 2000. Biodegradable modified polyaspartic polymers for corrosion and scale control. U.S. Pat. No. 6,022,401.

Thomaides, John S., Klein A. Rodrigues, and Paul M. Petersen. 1999. Amino acid copolymers having pendent polysaccharide moieties and uses thereof. U.S. Pat. No. 5,962,400.

Tamaya, H., Y. Harada, M. Ajioka, and T. Yamaguchi. 1996. Electrostatic charge-preventing hair preparations or cosmetics containing polyaspartic acid or its salts. Japanese Patent JP 08041445 A2.

Wicks, Douglas A., L. K. Gindin, P. E. Yeske, and E. H. Jonsson. 1997. Aspartate-functional polyhydantoin prepolymers and their use in coating compositions. U.S. Pat. No. 5,597,930: 1–12.

Willman, K. W., and J. M. Vandermeer. 1996. Detergent compositions with oleoyl sarcosinate and polymeric dispersing agent. H 1,514.

Wood, Louis L. and G. J. Calton. 1993. Copolymers of polyamino acids as tartar barrier agents. U.S. Pat. No. 5,266,305.

Wood, Louis L. and G. J. Calton. 1999. Copolymers of polyaspartic acid and polycarboxylic acids and polyamines. U.S. Pat. No. 6,001,956.

Wood, Louis L. and G. J. Calton. 1998. Method for odor reduction. U.S. Pat. No. 5,833,972.

Zalipsky, Samuel, M. C. Woodle, D. D. Lasic, and F. J. Martin. 1995. Lipid-polymer conjugates and liposomes. U.S. Pat. No. 5,395,619.

I claim:

1. A method or preparing a derivative of a copolymer containing copolymerized aspartate units and succinimide units which comprises:

heating to polymerize a comonomer mixture of aspartic acid and a salt of aspartic acid, which comonomer mixture was prepared by drying a solution of salt of aspartic acid having a cation which does not volatilize during the drying and a salt of aspartic acid having a cation which at least partially volatilizes to free aspartic acid during the drying to form a copolymer;

derivatizing said copolymer by reacting an amino group-containing compound, —OH group-containing compound or other nucleophilic group-containing compound with at least one succinimide unit of the copolymer;

wherein said derivatizing is conducted in an aqueous solution, an organic solvent or a mixture thereof.

2. The method of claim 1, wherein said amino group-containing compound, —OH group-containing compound or other nucleophilic group-containing compound is dispersed in the solution in the form of an emulsion.

3. The method of claim 1, wherein said derivatizing is conducted at a temperature of from 5 to 90° C.

4. The method of claim 1, wherein said derivatizing is conducted at a temperature of from 20 to 60° C.

5. The method of claim 1, wherein said derivatizing is conducted at a temperature of from 30 to 50° C.

6. The method of claim 1, wherein said derivatizing is conducted in an aqueous solution at a pH of from 8 to 11.

7. The method of claim 1, wherein said derivatizing is conducted in an aqueous solution at a pH of from 8 to 10.

8. The method of claim 1, wherein said organic solvent is apolar solvent or a polar solvent or nonpolar solvent.

9. The method of claim 8, wherein said polar solvent is an alcohol.

10. The method of claim 9, wherein said alcohol is isopropanol.

11. The method of claim 8, wherein said nonpolar solvent is selected from the group consisting of dimethyl formamide, dichloromethane and N-methyl-pyrolidone.

12. The method of claim 1, wherein said amino group containing compound is selected from the group consisting of a monoamino polyoxyalkylene, a monoamino siloxane, a monamino phosphonate, a monoamino sulfonate and an amino alcohol.

13. The method of claim 1, wherein said amino group containing compound is an amino acid.

14. The method of claim 13, wherein said amino acid is selected from the group consisting of leucine, serine, dihydroxyphenylalanine, phosphoserine and alanine.

15. The method of claim 1, wherein said —OH group containing compound is selected from the group consisting of a monomeric carbohydrate, a disaccharide, a polysaccharide and an oligomeric fragment of a polysaccharide.

16. The method of claim 15, wherein said disaccharide is selected from the group consisting of glucose, galactose, manose, lactose sucrose and a mixture thereof.

17. The method of claim 15, wherein said polysaccharide is selected from the group consisting of celluose, starch and amylase.

18. The method of claim 1 wherein said derivatizing is at a level of from 1 to 100% of the available succinimide units.

19. The method of claim 1 wherein said derivatizing is conducted by adding the amino group containing compound, —OH group-containing compound or other nucleophilic group containing compound to a solution of the comonomer.

20. The method of claim 1 wherein said derivatizing is conducted by adding the comonomer to a solution of the amino group containing compound, —OH group-containing compound or other nucleophilic group containing compound.

21. The dervatized copolymer containing copolymerized aspartate units and succinimide units prepared by the method of claim 1.

22. A method or preparing a mixture of aspartic acid and a salt of aspartic acid which comprises:
coprecipitating from solution containing a salt of aspartic acid having a cation which does not volatilize during the drying and a salt of aspartic acid having a cation which at least partially volatilizes to provide free aspartic acid during the drying; and
filtering and drying the mixture.

23. A method or preparing a comonomer mixture of aspartic acid and a salt of aspartic acid which comprises:
mixing maleic acid ammonia, a soluble nonalkali cationic salt and soluble alkali cationic salt to internally generate a combination of aspartic acid and aspartate salt comonomer mixture.

24. A method or preparing a mixture of aspartic acid and a salt of aspartic acid which comprises:
drying a solution of a salt of aspartic acid having a cation which does not volatilize during the drying and a salt of aspartic acid having a cation which at least partially volatilizes to provide free aspartic acid during the drying;
wherein said solution comprises an additional comonomer copolymerizable with the aspartic acid and salt of aspartic acid; and
wherein said additional comonomer is selected from the group consisting of alanine, ornithine, glycine, leucine, isoleucine, methionine, theronine, caprolactam, glucuronic acid, and a hydroxyl-containing carboxylate.

25. A method or preparing a mixture of aspartic acid and a salt of aspartic acid which comprises:
drying a solution of a salt of aspartic acid having a cation which does not volatilize during the drying and a salt of aspartic acid having a cation which at least partially volatilizes to provide free aspartic acid during the drying, and
wherein said cation which does not volatilize during drying is selected from the group consisting of an alkali metal, an alkaline earth metal and a transition metal.

26. A copolymer comprising polymerized aspartate units and succinimide units wherein said copolymer exhibits a molecular weight of from 300 to 5,000 daltons.

27. The copolymer of claim 26, wherein said copolymer exhibits a block copolymer structure, a graft copolymer structure, a linear structure or a branched structure.

28. A copolymer containing copolymerized aspartate units and succinimide units prepared by heating to polymerize a comonomer mixture of aspartic acid and a salt of aspartic acid, wherein said comonomer mixture was prepared by drying a solution of a salt of aspartic acid having a cation which does not volatilize during the drying and a salt of aspartic acid having a cation which at least partially volatilizes to free aspartic acid during the drying; and wherein said copolymer exhibits an amide peak in the region of 1600 $cm^{-1}$ and a carboxylate peak in the region of 1400 $cm^{-1}$ in an infrared spectrum.

29. The method of claim 24, wherein said hydroxyl-containing carboxylate is citric acid or malonic acid.

30. The copolymer of claim 26, further comprising a polyamine in an amount of from 1 to 50 mole %.

31. The copolymer of claim 30, wherein said copolymer exhibits a molecular weight of from 30 to 100,000 daltons.

32. A method or preparing a copolymer containing copolymerized aspartate units and succinimine units comprising:
heating to polymerize a comonomer mixture of aspartic acid and a salt of aspartic acid in the presence of a preformed polyaspartate, which comonomer mixture was prepared by drying a solution of a salt of aspartic acid having a cation which does not volatilize during the drying, salt of aspartic acid having a cation which at least partially volatilizes to free aspartic acid during the drying and a preformed polyaspartate.

33. The method of claim 32, wherein said preformed polyaspartate exhibits a molecular weight of from 1,000 to 100,000 daltons.

34. The method of claim 32, wherein said preformed polyaspartate exhibits a molecular weight of from 2,000 to 30,000 daltons.

35. The copolymer formed by the process of claim 32.

36. A copolymer comprising a mixture of aspartate units and succinimide units, said mixture exhibiting a molecular weight greater than 300 daltons.

37. The copolymer set forth in claim 36, wherein said copolymer exhibits a molecular weight from about 5000 to about 100,000 daltons.

38. The copolymer set forth in claim 36, wherein said copolymer exhibits a molecular weight greater than about 100,000 daltons.

39. An aspartate copolymer comprising monomer residues of (a) aspartate residues, which may be substituted at the side chain carboxyl, and (b) succinimide residues, and wherein said copolymer is characterized by (i) a molecular weight greater than 5000 Daltons, or (ii) a substantially linear structure and a molecular weight greater than 300 daltons, or (iii) water solubility and a molecular weight greater than 500 daltons, or any combination thereof.

40. The copolymer of claim 39, characterized by (i) a molecular weight of about 5000 to 100,000 daltons, or (ii) a substantially linear structure and a molecular weight of about 600 to about 100,000 daltons, or (iii) water solubility and a molecular weight of about 2000 to about 100,000 daltons, or any combination thereof.

41. The copolymer of claim 39, characterized by water solubility and a molecular weight of about 5000 to about 100,000 Daltons.

42. The copolymer of claim 41, having a substantially linear structure.

* * * * *

UNITED STATES PATENT AND TRADEMARK OFFICE
CERTIFICATE OF CORRECTION

PATENT NO. : 6,686,440 B2
DATED : February 3, 2004
INVENTOR(S) : Graham Swift

It is certified that error appears in the above-identified patent and that said Letters Patent is hereby corrected as shown below:

Title page,
Item [54], Title, "COMOMER" should read -- COMONOMER --.

Column 4,
Line 53, the sodium ion should be -- ($Na^+$) --.

Column 26,
Line 56, "(3.55 of $Na_2SO_4$ (Mw 142)" should read -- (3.55 g) of $Na_2SO_4$ (Mw 142) --;

Column 29,
Line 43, "and or" should read -- and/or --.

Column 36,
Line 35, "from 30 to 100,000 daltons" should read -- from 300 to 100,000 daltons --

Signed and Sealed this

Twentieth Day of April, 2004

JON W. DUDAS
*Acting Director of the United States Patent and Trademark Office*